US010492794B2

(12) United States Patent
Ikeda et al.

(10) Patent No.: US 10,492,794 B2
(45) Date of Patent: Dec. 3, 2019

(54) CLIP CARTRIDGE

(71) Applicant: SUMITOMO BAKELITE CO., LTD., Shinagawa-ku (JP)

(72) Inventors: Masao Ikeda, Akita (JP); Takuya Hayashi, Akita (JP); Etsuro Yamabe, Akita (JP); Hideaki Matsunami, Akita (JP); Wataru Otsuka, Akita (JP); Tetsuro Abe, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 0 days.

(21) Appl. No.: 16/078,449

(22) PCT Filed: Feb. 23, 2017

(86) PCT No.: PCT/JP2017/006792
§ 371 (c)(1),
(2) Date: Aug. 21, 2018

(87) PCT Pub. No.: WO2017/146138
PCT Pub. Date: Aug. 31, 2017

(65) Prior Publication Data
US 2019/0046205 A1 Feb. 14, 2019

(30) Foreign Application Priority Data

Feb. 23, 2016 (JP) ................... 2016-032278

(51) Int. Cl.
*A61B 17/122* (2006.01)
*A61B 17/128* (2006.01)
(Continued)

(52) U.S. Cl.
CPC ........ *A61B 17/1222* (2013.01); *A61B 17/122* (2013.01); *A61B 17/1285* (2013.01);
(Continued)

(58) Field of Classification Search
CPC .............. A61B 17/122; A61B 17/1222; A61B 17/1285; A61B 2017/0053; A61B 2017/12
See application file for complete search history.

(56) References Cited

U.S. PATENT DOCUMENTS

2011/0245855 A1 10/2011 Matsuoka et al.
2017/0020531 A1 1/2017 Naveed et al.

FOREIGN PATENT DOCUMENTS

EP 1 547 529 A1 6/2005
EP 1 818 020 A1 8/2007
(Continued)

OTHER PUBLICATIONS

JP-2009125547-A English translation.*
(Continued)

*Primary Examiner* — Todd J Scherbel
*Assistant Examiner* — Brooke Labranche
(74) *Attorney, Agent, or Firm* — Oblon, McClelland, Maier & Neustadt, L.L.P.

(57) ABSTRACT

According to the present invention, there is provided a clip cartridge in which a clip having a structure enabling a user to easily perform a series of procedures can be easily and reliably mounted on a treatment instrument body. A clip cartridge (200) according to the present invention includes an inner case (30) that has a first accommodation region (32) for accommodating a clip (110), and an outer case (40) that has an elongated insertion hole (43) into which a treatment instrument body (90) is inserted, and a second accommodation region (42) which accommodates the inner case (30) so as to be movable. The treatment instrument body (90) is inserted into the insertion hole (43), and an operation wire is pressed forward so that a distal connection portion and a diameter enlargement portion of the sleeve protrude from the sheath to a distal side and enter the second accommo- (Continued)

dation region (42), and so that a diameter enlargement portion is elastically enlarged in diameter. The operation wire is further pressed so as to bring a distal connection portion and the clip (110) into a mutually connected state. The operation wire is pulled so that the inner case (30) moves backward relative to the outer case (40) so as to press the sleeve backward, thereby drawing the diameter enlargement portion into the sheath while reducing the diameter enlargement portion in diameter.

20 Claims, 11 Drawing Sheets

(51) Int. Cl.
 *A61B 17/00* (2006.01)
 *A61B 17/12* (2006.01)
(52) U.S. Cl.
 CPC ............... *A61B 2017/0053* (2013.01); *A61B 2017/12004* (2013.01)

(56) References Cited

FOREIGN PATENT DOCUMENTS

| | | | |
|---|---|---|---|
| JP | 2004-121485 A | | 4/2004 |
| JP | 2008113673 A | * | 5/2008 |
| JP | 2009-11769 A | | 1/2009 |
| JP | 2009-125547 A | | 6/2009 |
| JP | 2009125547 A | * | 6/2009 |
| JP | 3159939 U | | 6/2010 |
| JP | 2011-206488 A | | 10/2011 |
| JP | 2015-43858 A | | 3/2015 |
| JP | 2015-149997 A | | 8/2015 |
| WO | WO 2006/062019 A1 | | 6/2006 |

OTHER PUBLICATIONS

JP-2008113673-A English translation.*
International Search Report dated May 23, 2017 in PCT/JP2017/006792 filed Feb. 23, 2017.

* cited by examiner

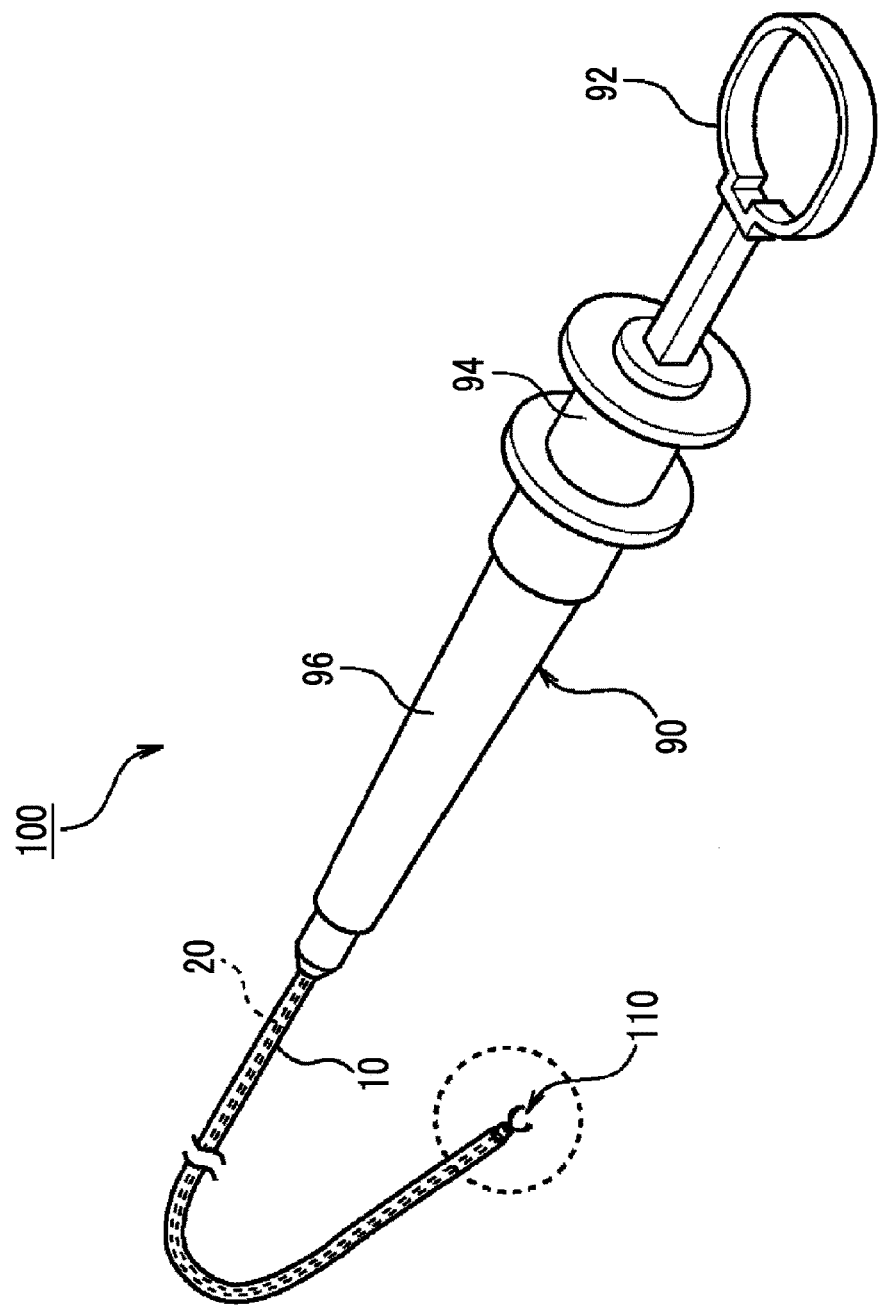

CLIP CARTRIDGE

TECHNICAL FIELD

The present invention relates to a clip cartridge.

BACKGROUND ART

There is provided an endoscopic clip device which excises a living body tissue in a body lumen by using an endoscope, and which ligates an excised site and performs hemostasis thereon. With regard to this endoscopic clip device, PTL 1 discloses the following clip cartridge (case in PTL 1). An arrowhead hook of a distally located portion of an operation wire disposed in a treatment instrument body is inserted into and connected to a connection member of a proximal portion of a clip. In this manner, the clip is brought into a state where the clip is connected to the treatment instrument body.

In order to ligate the living body tissue by using the endoscopic clip device of PTL 1, a pulling operation of the operation wire is performed in a state where the arrowhead hook is inserted into the connection member. If the operation wire is further strongly pulled in a state where the living body tissue is ligated, a reduced diameter portion of the connection member is broken, and the clip is allowed to indwell the inside of the body lumen in a state where the living body tissue is ligated.

The broken connection member is collected in a state of being connected to the arrowhead hook. Thereafter, the broken connection member is detached from the arrowhead hook and is discarded.

CITATION LIST

Patent Literature

[PTL 1] Japanese Unexamined Patent Application, First Publication No. 2004-121485

SUMMARY OF INVENTION

Technical Problem

As described above, in the endoscopic clip device of PTL 1, after the clip indwells the inside of the body lumen, it is necessary to collect the broken connection member, to detach the broken connection member from the arrowhead hook and to discard the broken connection member. Therefore, a series of procedures are troublesome, and there is a possibility that infection may occur.

The present invention is made in view of the above-described problems, and an object thereof is to provide a clip cartridge in which a clip having a structure enabling a user to easily perform a series of procedures can be easily and reliably mounted on a treatment instrument body.

Solution to Problem

According to the present invention, there is provided a clip cartridge used for connecting a clip to an elongated treatment instrument body. The clip includes a plurality of arms for gripping a living body tissue and a clip body having a locking portion disposed on a proximally located side of the arms. The treatment instrument body has an elongated sheath, an operation wire which is inserted into the sheath so as to be movable forward and backward and in which a distal connection portion is disposed in a distally located portion, a cylindrical sleeve which is capable of being accommodated inside the sheath and which accommodates the distal connection portion, and a transmission portion which transmits a forward movement force and a backward movement force from the operation wire to the sleeve. The sleeve has a diameter enlargement portion which is elastically self-openable, and a cylindrical sleeve body which is disposed on a proximally located side from the diameter enlargement portion and whose radial rigidity is higher than that of the diameter enlargement portion. The clip cartridge includes an inner case that has a first accommodation region for accommodating the clip, and an outer case that has an elongated insertion hole into which the treatment instrument body is inserted, and a second accommodation region which communicates with a distal end of the insertion hole and which accommodates the inner case so as to be movable to a distal side and a proximal side. In a state where the treatment instrument body is inserted into the insertion hole, the operation wire is pressed forward so that the distal connection portion and the diameter enlargement portion of the sleeve protrude from the sheath to a distal side and enter a region between the inner case in the second accommodation region and the insertion hole, and so that the diameter enlargement portion is elastically enlarged in diameter. The operation wire is further pressed forward so that the distal connection portion moves forward relative to the sleeve, thereby causing the distal connection portion to protrude from the sleeve to the distal side and bringing the distal connection portion and the locking portion into a mutually connected state. The operation wire is pulled to a proximal side in the mutually connected state so that the inner case moves backward relative to the outer case inside the second accommodation region and the inner case presses the sleeve backward, thereby drawing the diameter enlargement portion into the sheath while reducing the diameter enlargement portion in diameter.

Advantageous Effects of Invention

According to the present invention, a clip having a structure enabling a user to easily perform a series of procedures can be easily and reliably mounted on a treatment instrument body.

BRIEF DESCRIPTION OF DRAWINGS

FIG. 6 is a perspective view illustrating an example of an endoscopic clip device.

DESCRIPTION OF EMBODIMENTS

Figure 1:
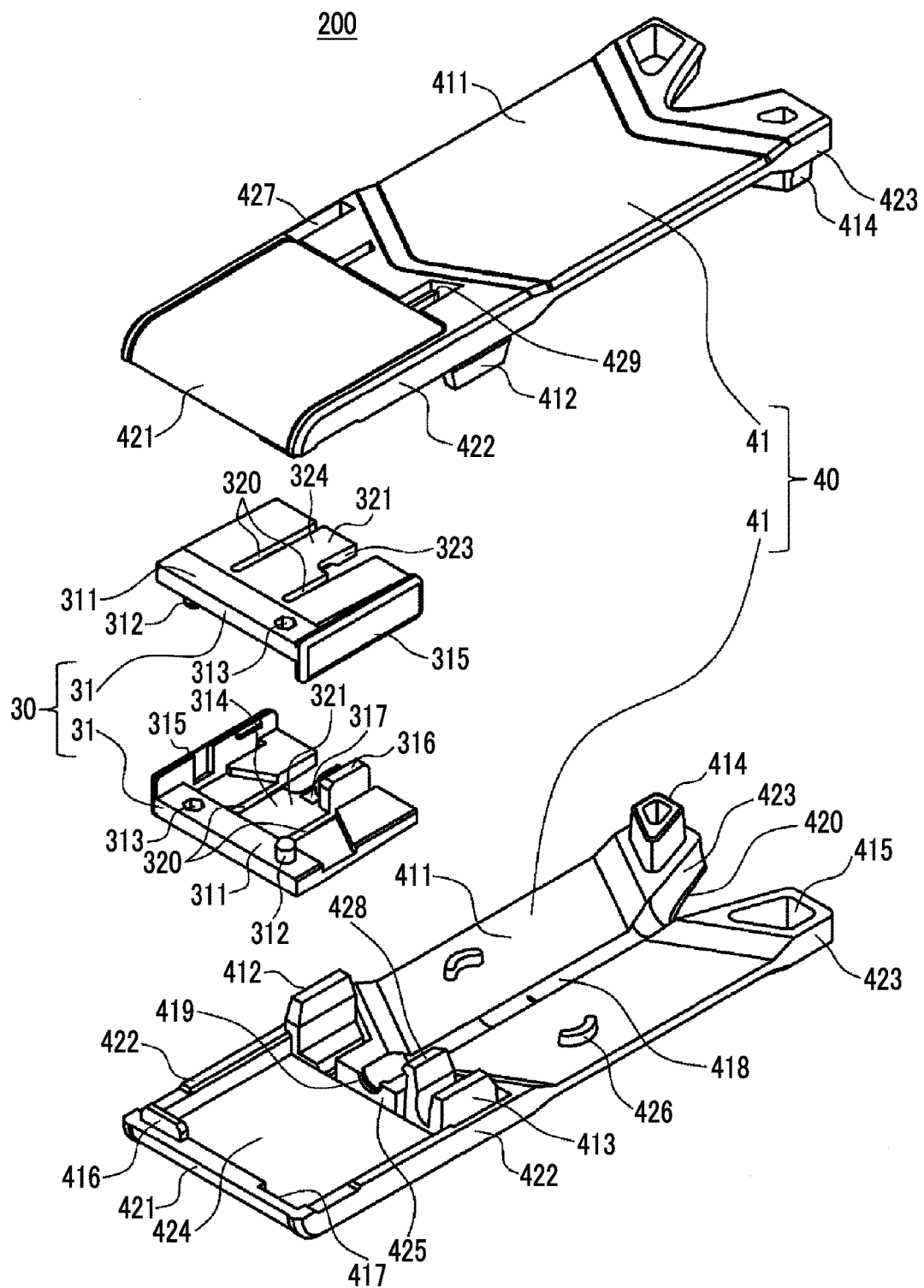
FIG. 1 is an exploded perspective view of a clip cartridge according to an embodiment.

Hereinafter, an embodiment according to the present invention will be described with reference to the drawings. In all of the drawings, the same reference numerals will be given to the same configuration elements, and repeated description will be appropriately omitted.

Figure 2:
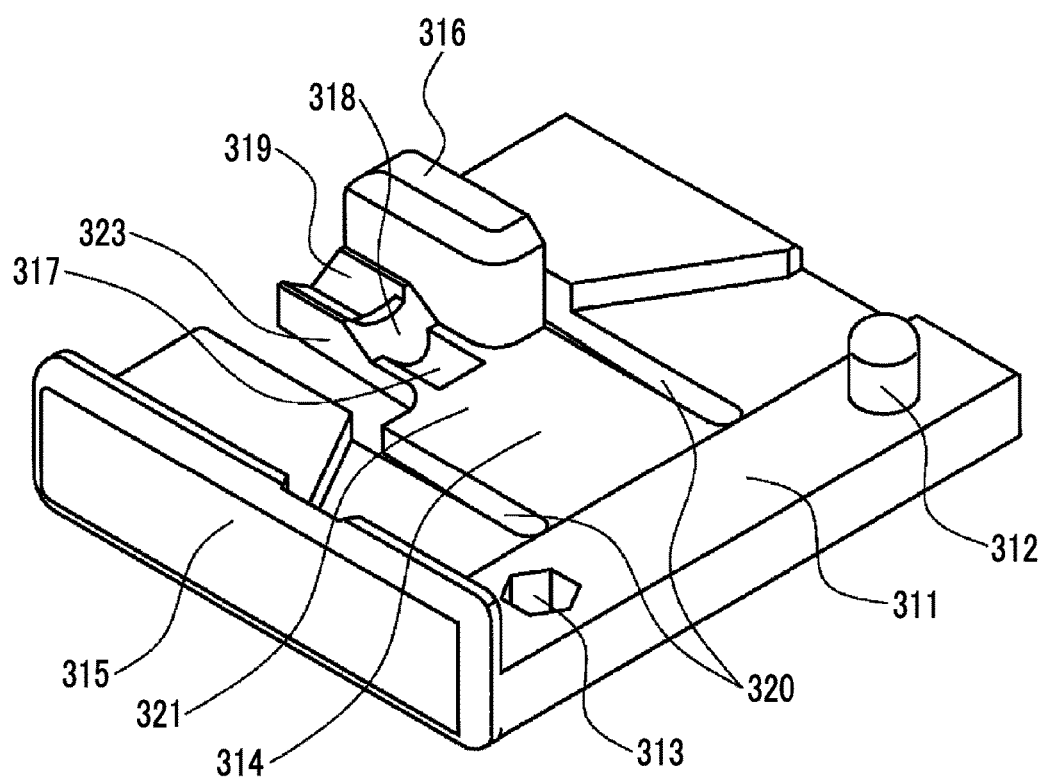
FIG. 2 is a perspective view of an inner case configuration component configuring an inner case of the clip cartridge.
Figure 3:
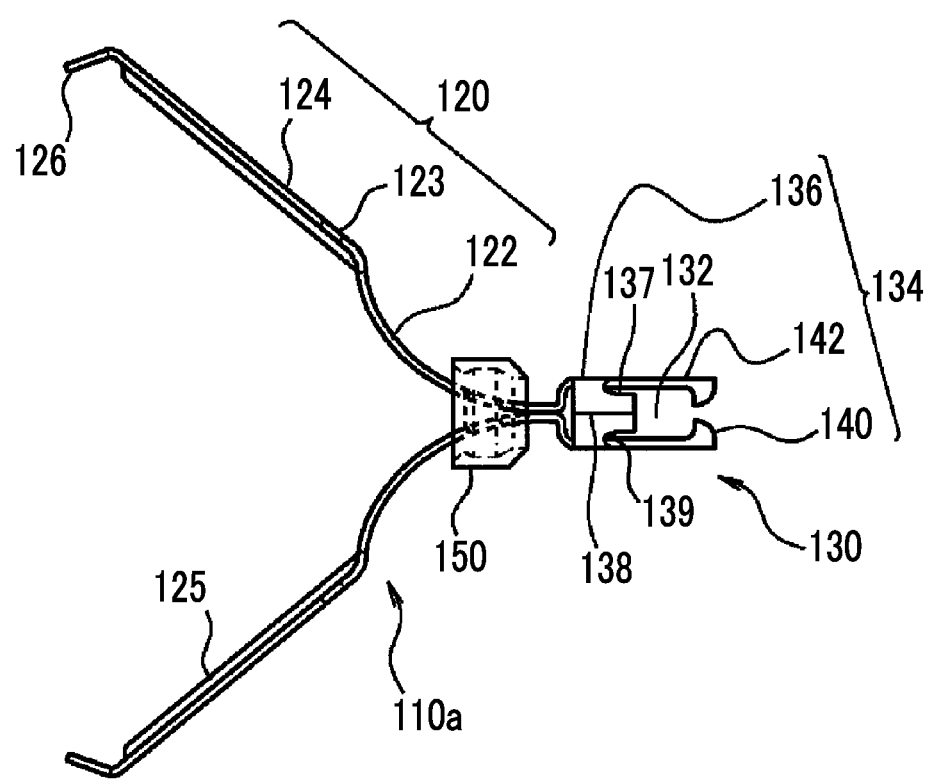
FIG. 3 is a plan view of a clip in an open arm state.

FIG. 1 is an exploded perspective view of a clip cartridge 200 according to the embodiment. FIG. 2 is a perspective view of an inner case configuration component 31 configuring an inner case 30 (FIG. 1) of the clip cartridge 200. FIG. 3 is a plan view of a clip 110 in an open arm state.

Figure 4:
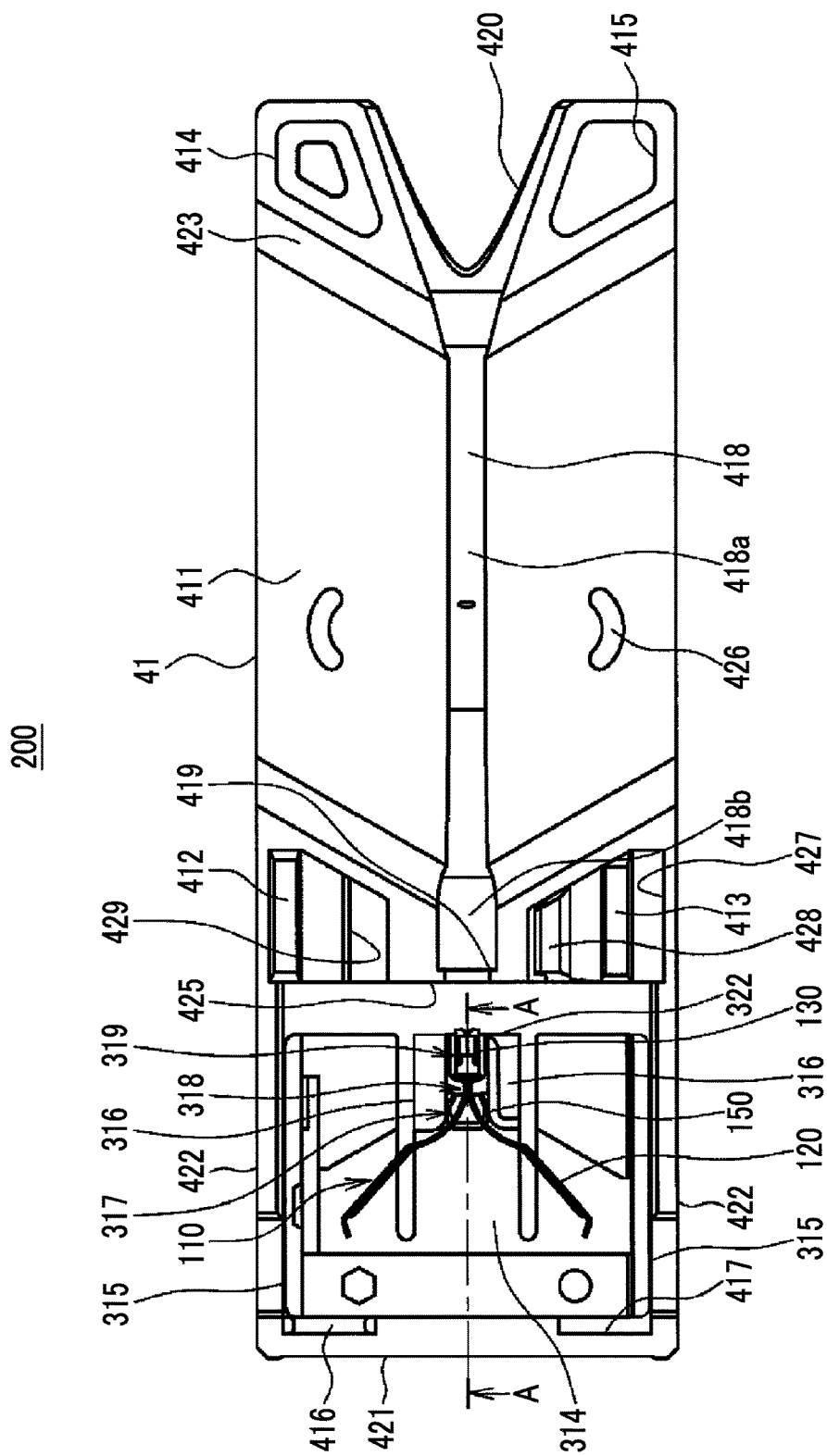
FIG. 4 is a plan view illustrating a state where the clip is accommodated in the clip cartridge.
Figure 5:
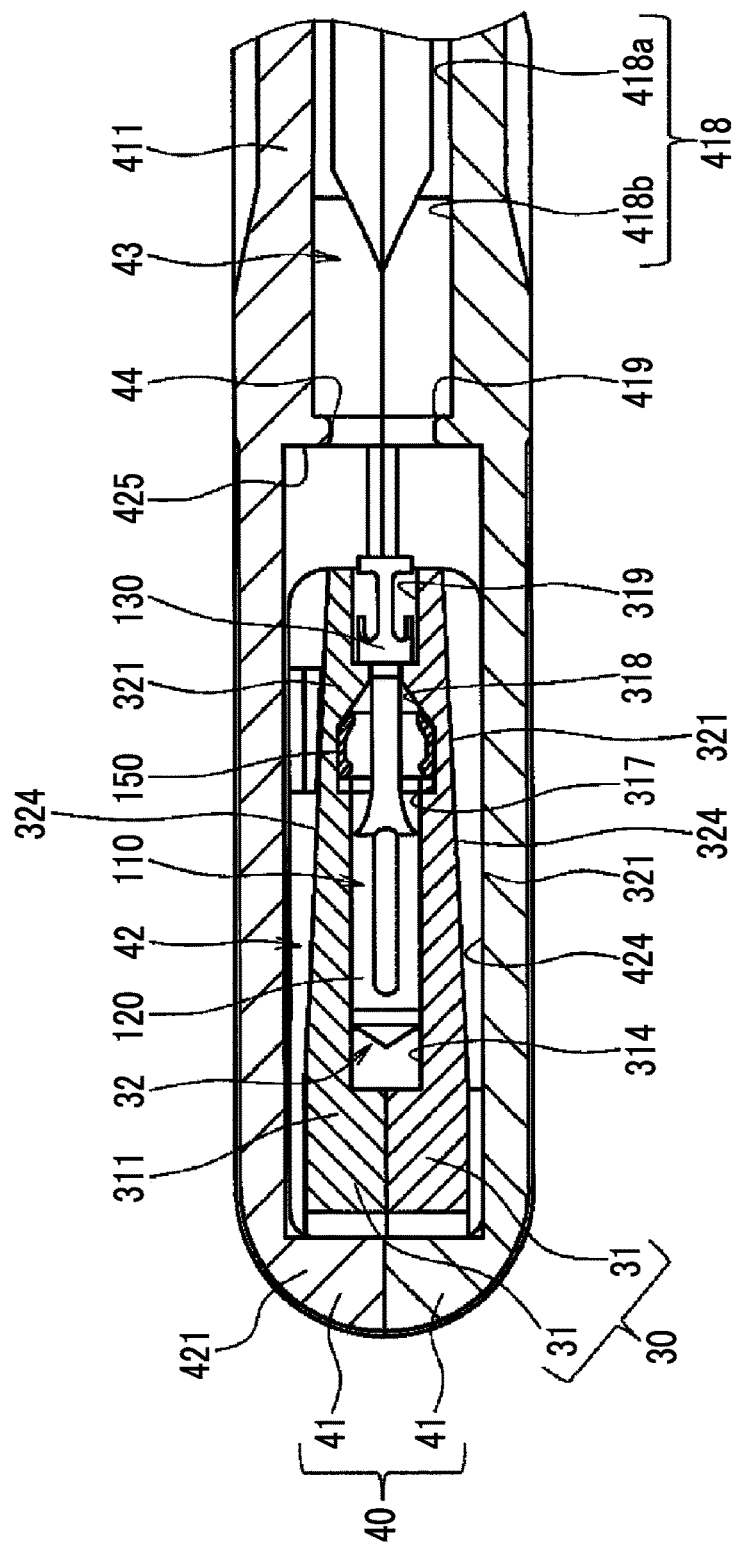
FIG. 5 is a side sectional view taken along line A-A in FIG. 4.

FIG. 4 is a plan view illustrating a state where the clip 110 is accommodated in the clip cartridge 200. In FIG. 4, in a pair of outer case configuration components 41 configuring an outer case 40, the outer case configuration component 41 on an upper side is omitted in the illustration. In a pair of inner case configuration components 31 configuring the inner case 30, with regard to the inner case configuration component 31 on an upper side, only a side wall 315 (to be described later) and an adjacent wall 316 (to be described later) are illustrated. FIG. 5 is a side sectional view taken along line A-A in FIG. 4. FIG. 6 is a perspective view illustrating an example of an endoscopic clip device (hereinafter, sometimes abbreviated as a clip device) 100.

FIGS. 7A, 7B to 10A, 10B, and 10C are schematic views for describing a series of operations for mounting the clip 110 on a treatment instrument body 90 of the endoscopic clip device 100.

Figure 11A:
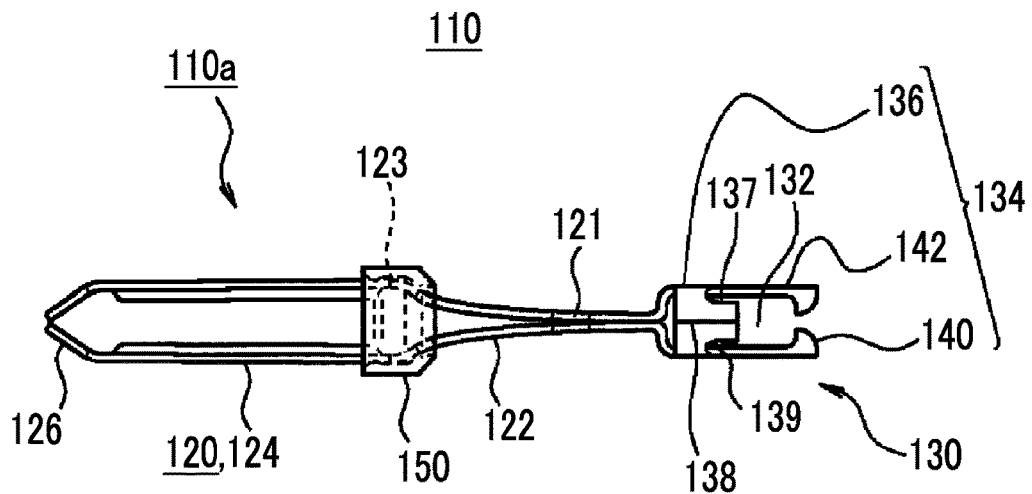
FIG. 11A is a plan view illustrating the clip in a closed arm state.
Figure 11B:
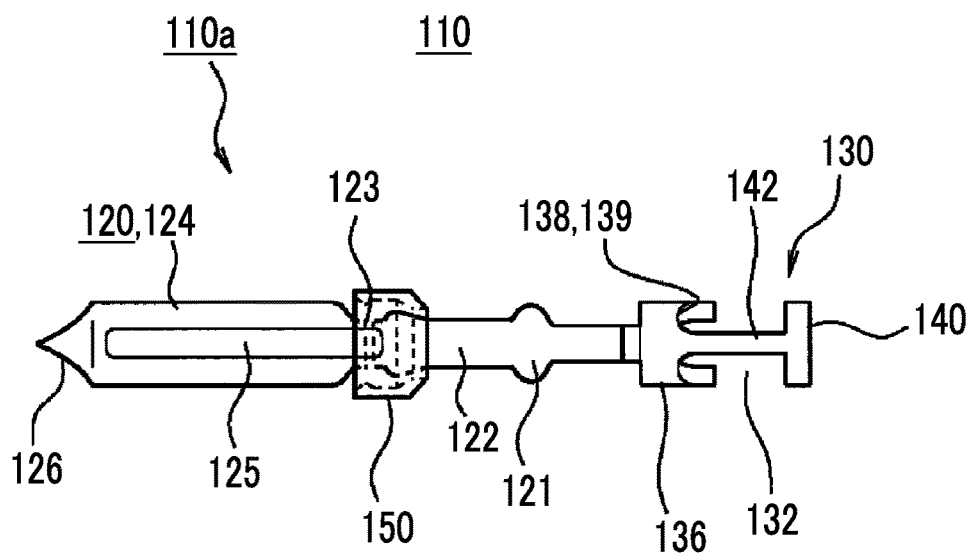
FIG. 11B is a side view illustrating the clip in the closed arm state.

FIG. 11A is a plan view illustrating the clip 110 in a closed arm state, and FIG. 11B is a side view.

In the present specification, unless otherwise specified, an "axial direction" means a forward/backward movement direction of an operation wire 20 (refer to FIGS. 7A and 7B) of the treatment instrument body 90. In addition, unless otherwise specified, a "cross section" means a longitudinal cross section in which the endoscopic clip device 100 is cut in the axial direction.

Unless otherwise specified, a "distally located side (or a distally located portion)" is referred to as a side far away from an operator of the endoscopic clip device 100 in the endoscopic clip device 100, the clip 110 mounted thereon, or the clip cartridge 200, and specifically means a side having a distal end (claw 126) of an arm 120 of the clip 110. In addition, unless otherwise specified, a "proximally located side (or a proximally located portion)" means a side close to the operator in the endoscopic clip device 100, the clip 110, or the clip cartridge 200. In addition, movement of a configuration element of the endoscopic clip device 100, the clip 110, or the clip cartridge 200 to the distally located side will be referred to as forward movement, and reverse movement to the proximally located side will be referred to as backward movement in some cases. Furthermore, the "distal side (or the distal end)" is used synonymously with the "distally located side (or the distally located portion", and the "proximal side (or the proximal end)" is used synonymously with the "proximally located side (or the proximally located portion)".

In addition, a direction from the proximal side to the distal side or a direction from the distal side to the proximal side will be referred to as a distal/proximal direction or a forward/backward direction.

In addition, as will be described later, the clip cartridge 200 is formed in a flat shape. Then, a direction orthogonal to both the distal/proximal direction and a thickness direction of the clip cartridge 200 will be referred to as a width direction.

The clip cartridge 200 according to the present embodiment is the clip cartridge 200 used for connecting the clip 110 to the elongated treatment instrument body 90.

As illustrated in FIG. 3, the clip 110 includes a clip body 110a having a plurality of arms 120 for gripping a living body tissue and a locking portion 130 disposed on the proximal side of the arm 120.

As illustrated in any one of FIGS. 6 to 10A, 10B, and 10C, the treatment instrument body 90 has an elongated sheath 10, an operation wire 20 which is inserted into the sheath 10 so as to be movable forward and backward and in which a distal connection portion 50 is disposed in a distally located portion, a cylindrical sleeve (diameter reduction sleeve 70) which can be accommodated inside the sheath 10 and which accommodates the distal connection portion 50, and a transmission portion (for example, an elastic portion 80) which transmits a forward movement force and a backward movement force to the sleeve from the operation wire 20.

The sleeve has an elastically self-openable diameter enlargement portion 72 and a cylindrical sleeve body 76 which is disposed on a proximally located side from the diameter enlargement portion 72 and whose radial rigidity is higher than that of the diameter enlargement portion 72. Here, the description that the radial rigidity of the sleeve body 76 is higher than the radial rigidity of the diameter enlargement portion 72 means that when forces acting radially inward are respectively applied to the sleeve body 76 and the diameter enlargement portion 72, the amount of radially inward displacement caused by elastic deformation is smaller in the sleeve body 76 than in the diameter enlargement portion 72.

As illustrated in any one of FIGS. 1, 4, 5, 7A, 7B to 10A, 10B, and 10C, the clip cartridge 200 includes the inner case 30 and the outer case 40. The inner case 30 has a first accommodation region 32 which accommodates the clip 110. In addition, the outer case 40 has an elongated insertion hole 43 into which the treatment instrument body 90 is inserted, and a second accommodation region 42 which communicates with a distal end of the insertion hole 43 and which accommodates the inner case 30 so as to be movable to the distal side and the proximal side.

As illustrated in FIGS. 7A, 7B, 8A, and 8B, the operation wire 20 is pressed forward in a state where the treatment instrument body 90 is inserted into the insertion hole 43. In this manner, the distal connection portion 50 and the diameter enlargement portion 72 of the sleeve protrude from the sheath 10 to the distal side, and enter a region between the inner case 30 and the insertion hole 43 in the second accommodation region 42. The diameter enlargement portion 72 is elastically enlarged in diameter.

Figure 8A:
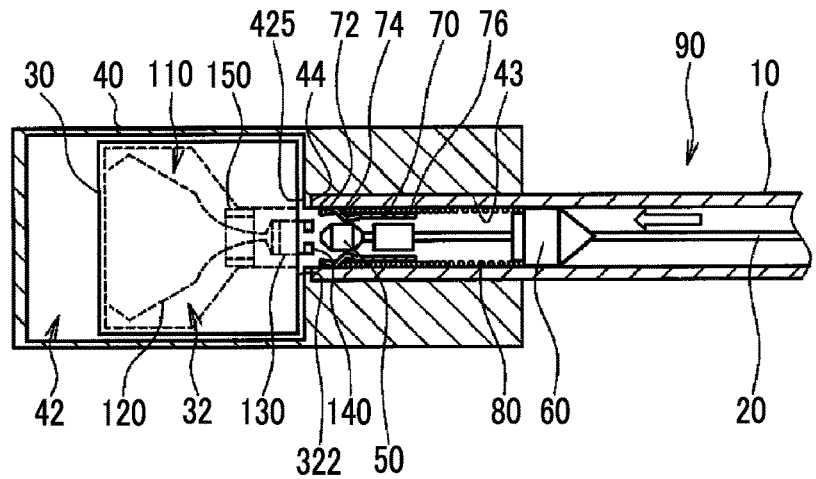
FIG. 8A is a schematic view for describing a series of operations for mounting the clip on the treatment instrument body of the endoscopic clip device.
Figure 8B:
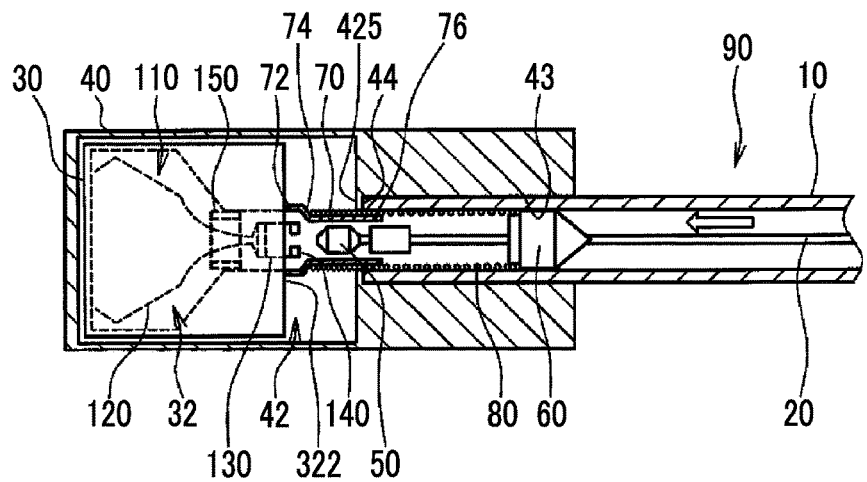
FIG. 8B is a schematic view for describing a series of operations for mounting the clip on the treatment instrument body of the endoscopic clip device.
Figure 8C:
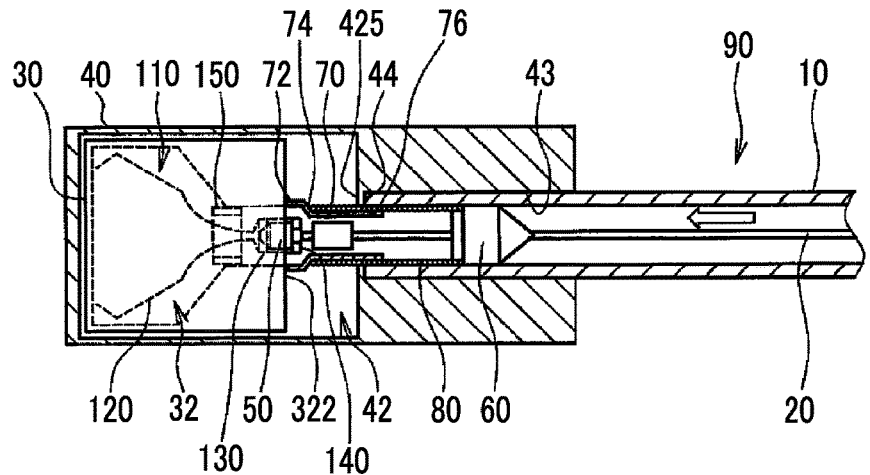
FIG. 8C is a schematic view for describing a series of operations for mounting the clip on the treatment instrument body of the endoscopic clip device.

As illustrated in FIG. 8C, the operation wire 20 is further pressed forward so that the distal connection portion 50 moves forward relative to the sleeve. In this manner, the distal connection portion 50 protrudes from the sleeve to the distal side, and the distal connection portion 50 and the locking portion 130 are brought into a mutually connected state.

Figure 9A:
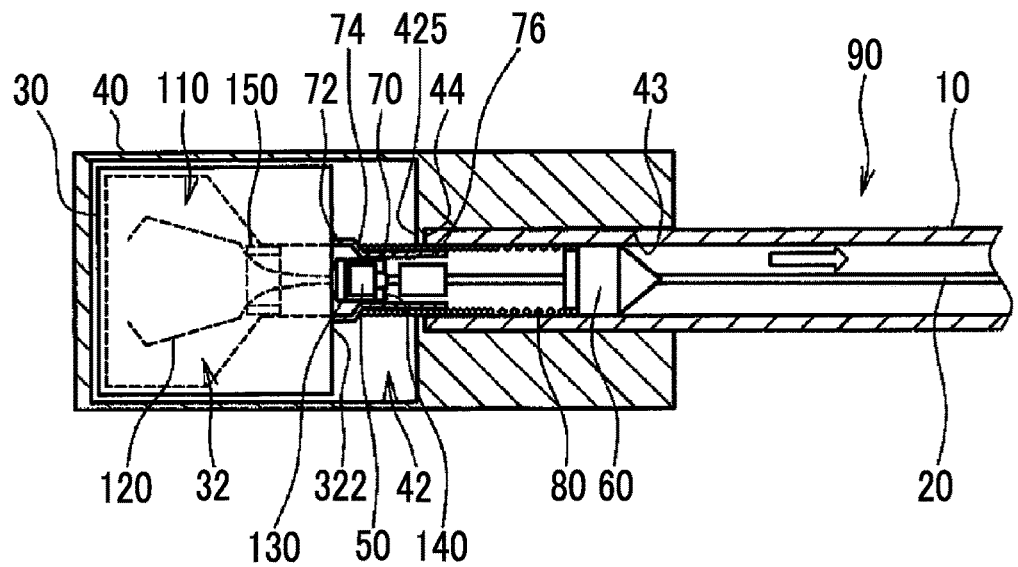
FIG. 9A is a schematic view for describing a series of operations for mounting the clip on the treatment instrument body of the endoscopic clip device.
Figure 9B:
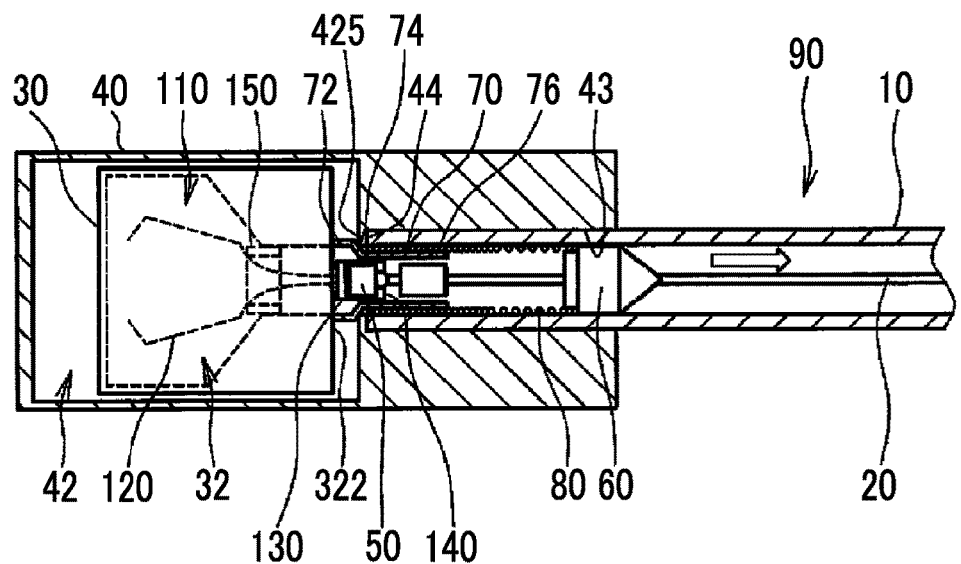
FIG. 9B is a schematic view for describing a series of operations for mounting the clip on the treatment instrument body of the endoscopic clip device.
Figure 10A:
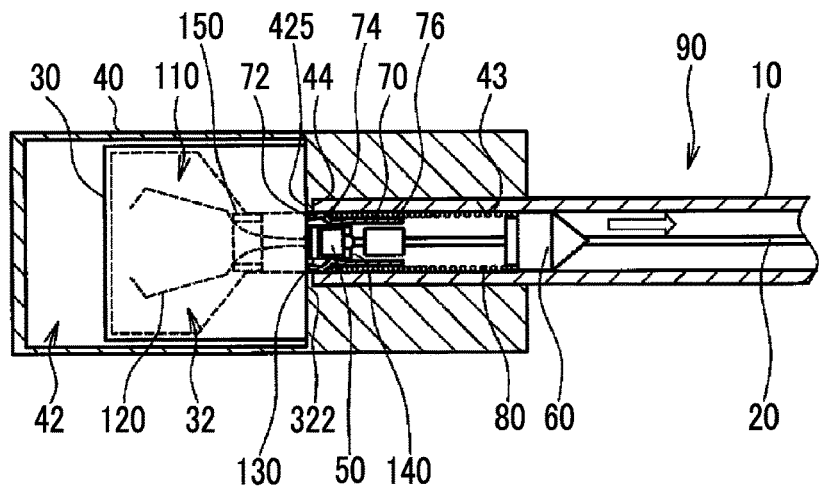
FIG. 10A is a schematic view for describing a series of operations for mounting the clip on the treatment instrument body of the endoscopic clip device.

As illustrated in FIGS. 9A, 9B, and 10A, the operation wire 20 is pulled to the proximal side in the mutually connected state. In this manner, the inner case 30 moves backward relative to the outer case 40 inside the second accommodation region 42, and the inner case 30 presses the sleeve backward, thereby drawing the diameter enlargement portion 72 into the sheath 10 while reducing the diameter enlargement portion 72 in diameter.

A specific structure of the treatment instrument body 90 included in the clip device 100 is not particularly limited. FIG. 6 illustrates the treatment instrument body 90 including a finger ring 92, a slider 94, and a main body shaft 96. For example, a user of the clip device 100 hooks a finger (for example, a thumb) on the finger ring 92. In a state where the user pinches the slider 94 with other fingers (for example, an index finger and a middle finger), the user performs an operation by relatively moving the slider 94 to the main body shaft 96. In this manner, the operation wire 20 connected to the slider 94 is moved forward and backward inside the sheath 10. In addition, the treatment instrument body 90 is entirely rotated around the axis, thereby rotating the operation wire 20 together with the slider 94. In a case where the sheath 10 is in close contact with a wall surface of a forceps hole of an endoscope, the operation wire 20 is axially rotated inside the sheath 10. Hereinafter, the description that the treatment instrument body 90, the operation wire 20, and the clip 110 are axially rotated is referred to as "torque rotation" in some cases.

The clip device 100 is used by being inserted into the forceps hole (not illustrated) of the endoscope in a state where the clip 110 is connected to the distal end of the operation wire 20. Specifically, the clip device 100 can be used as follows. The sheath 10 is inserted from the proximally located side into the forceps hole of the endoscope indwelling the inside of a body lumen, and the distally located portion of the sheath 10 is protruded from a distally located opening of the forceps hole. The clip 110 is further exposed from the sheath 10 so as to ligate a living body tissue. The living body tissue to be ligated can include a body tube such as a blood vessel, in addition to a mucosal wall such as a treatment target site of endoscopic submucosal dissection (ESD).

The clip 110 ligates the living body tissue, and can perform treatment, for example, such as hemostasis, colporrhaphy, and marking by ligating the living body tissue with the arms 120. The arms 120 have a self-openable force, and the arms 120 in a closed arm state are protruded from the sheath 10 as described later. In this manner, the arms 120 are naturally opened and brought into an open arm state. Here, "self-opening" means an attempt to open itself by repelling against an external closing force.

The clip 110 includes a clamping ring 150 into which the plurality of arms 120 are collectively inserted, in addition to the clip body 110a having the plurality of arms 120 and the locking portion 130. The clamping ring 150 moves to the distal side of the arm 120 relative to the arm 120. In this manner, a configuration is adopted so that the respective distal ends (claws 126) of the plurality of arms 120 are brought into a mutually closed state.

More specifically, the clip 110 includes a pair of the arms 120 facing each other.

The pair of arms 120 respectively include a proximal portion 122 which protrudes from the locking portion 130 toward the distally located side (left side in FIG. 3) and an arm body 124 which is connected to the distally located side of the proximal portion 122. The proximal portion 122 is bent outward and toward the distally located side.

Here, the description "outward" means a direction away from an axis of the operation wire 20 or an extension line of the axis. For example, the description represents an outward direction in a radial direction. The description "inward" means a direction closer to the axis of the operation wire 20 or the extension line of the axis. For example, the description represents an inward direction in the radial direction.

The arm body 124 is linearly formed, and the distal end of the arm body 124 has the claw 126. The arm body 124 and the claw 126 are gripping regions for mainly gripping the living body tissue. The claw 126 protrudes inward from the pair of arm bodies 124, and digs into the living body tissue, thereby improving a gripping force of the clip 110.

The arms 120 are bent at a boundary between the proximal portion 122 and the arm body 124. At the boundary, a narrowed portion 123 is formed in which a width dimension of the arms 120 is locally reduced (refer to FIG. 11B).

As illustrated in FIG. 3, the locking portion 130 and the pair of arms 120 are integrally molded so as to configure the clip body 110a. That is, one of the claw 126, the arm body 124, and the proximal portion 122 and the other one of the claw 126, the arm body 124, and the proximal portion 122 are seamlessly and continuously formed via the locking portion 130.

More specifically, a metal plate is punched out, pressed, and bent so as to prepare the clip body 110a including the pair of arms 120 and the locking portion 130 which are integrated with each other. As an example, the metal material can include stainless steel, titanium, or a titanium alloy, but the metal material is not limited thereto. In addition, the above-described metal material may be subjected to corrosion-resistant coating treatment.

A reinforcement portion 125 is formed in the arm body 124 by pressing (embossing) a portion of the center in the width direction (refer to FIG. 11B). Since the reinforcement portion 125 is formed, the thickness dimension of the arm body 124 increases (refer to FIGS. 3 and 11A), and bending rigidity of the arm body 124 is improved. In this manner, a strong gripping force for the living body tissue can be obtained. The reinforcement portion 125 is continuously formed in the arm body 124 from the distal portion excluding the claw 126 to the proximal portion leading to the narrowed portion 123.

The clamping ring 150 of the clip 110 is mounted on the arm 120 so as to be movable forward and backward. The clamping ring 150 moved to the distally located side relative to the arm 120. In this manner, the arms 120 in an open arm state (refer to FIG. 3) can be can be clamped against the self-openable force by the clamping ring 150. In this manner, the arms 120 are brought into a closed arm state (refer to FIGS. 11A and 11B). In addition, the clamping ring 150 is moved backward relative to the arm 120. Accordingly, the arms 120 are open using the self-openable force. The annular clamping ring 150 may have an entirely annular shape in which the entire circumferential surface is continuous in the circumferential direction, or may have a partially annular shape in which a notch or a slit is partially disposed in the circumferential direction.

The arm body 124 of the arm 120 is formed to be thicker than the proximal portion 122 or the narrowed portion 123, thereby restricting the clamping ring 150 in moving forward to the arm body 124 over the narrowed portion 123. In addition, the proximal portion 122 has a widened portion 121 which is partially formed to be thick. An inner diameter of the proximally located side of the clamping ring 150 is smaller than the width dimension of the widened portion 121. Therefore, the clamping ring 150 is restricted in moving to the proximally located side of the clip 110 over the widened portion 121. The clamping ring 150 moves forward to and backward from the arm 120 in a length region between the widened portion 121 and the arm body 124. Then, the clamping ring 150 is fitted to the narrowed portion 123. In this manner, the clamping ring 150 is locked to the arm 120, thereby locking the clip 110 in a closed arm state.

The locking portion 130 of the clip 110 has an accommodation portion 134 internally having a space 132 for accommodating the distal connection portion 50 (refer to FIG. 7A) of the distal end of the operation wire 20, and a protruding portion 140 formed to protrude inward on the proximal side of the accommodation portion 134. The accommodation portion 134 accommodates the distal connection portion 50 inside the space 132, thereby connecting the clip 110 and the operation wire 20 to each other.

The protruding portion 140 is a claw which is elastically deformed and opened so as to be spread out by the distal connection portion 50, and which is elastically restored so as to engage with and hold the distal connection portion 50.

The protruding portion 140 is disposed on the proximally located side of the accommodation portion 134, and closes the space 132 so as to be partially or entirely openable. A shape, position, and size of the protruding portion 140 are not particularly limited. For example, the accommodation portion 134 may be annularly formed, and the protruding portion 140 may be formed to protrude inward in the radial direction from the circumferential surface of the annular accommodation portion 134. Alternatively, as described below, the accommodation portion 134 may be configured to include an annular base 136 and a projection piece 142 protruding from the base 136 to the proximally located side, and the protruding portion 140 may be formed in the distal end of the projection piece 142.

The locking portion 130 includes the base 136 connected to the proximal end of the arm 120, and a plurality of projection pieces 142 projecting from the base 136 to the proximal side so as to configure the accommodation portion 134. The protruding portions 140 are respectively formed in the distal portions on the proximally located sides of the projection pieces 142.

The distal connection portion 50 of the operation wire 20 is accommodated in the space 132 surrounded by the base 136, the projection piece 142, and the protruding portion 140. The inner diameter of the base 136 is smaller than the maximum outer diameter of the distal connection portion 50, and restricts forward movement of the distal connection portion 50. The protruding portion 140 restricts backward movement of the distal connection portion 50 accommodated in the space 132. The distal connection portion 50 accommodated in the space 132 may be constrained in the distal/proximal direction by the base 136 and the protruding portion 140, and may be restricted in moving forward and backward inside the space 132. Alternatively, the distal connection portion 50 may be slightly movable forward and backward in the axial direction inside the space 132.

Figure 7A:
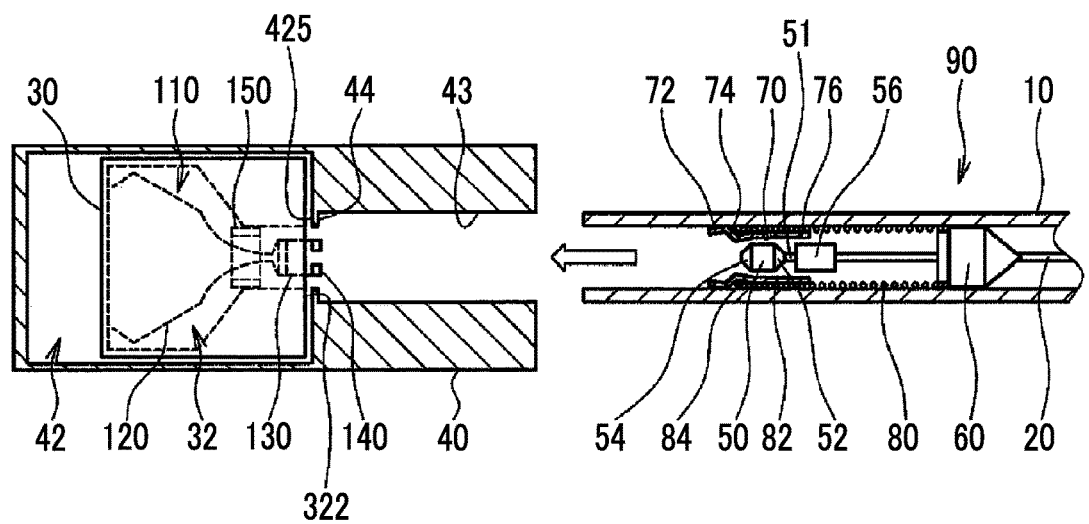
FIG. 7A is a schematic view for describing a state prior to mounting in a series of operations for mounting a clip on a treatment instrument body of the endoscopic clip device.

Here, in a case of the present embodiment, the distal connection portion 50 has a block shape. The description that the distal connection portion 50 has the "block shape" means the following. The distal connection portion 50 is thicker than the locking portion 130, the distal connection portion 50 is connected to the locking portion 130, and the distal connection portion 50 is removed from the locking portion 130. In this case, the deformation of the distal connection portion 50 is sufficiently smaller than the deformation of the locking portion 130. A specific shape of the block-shaped distal connection portion 50 is not particularly limited. As illustrated in FIG. 7A, the shape may be formed so that the distally located side portion and the proximally located side portion are respectively reduced in diameter toward the distally located portion and the proximally located portion. In addition to this shape, the shape may be columnar or spherical.

For example, a cross-sectional shape of the distal connection portion 50 is a polygonal shape, and preferably has a regular polygonal cross section. As an example, the distal connection portion 50 has a regular hexagonal cross section.

The plurality of projection pieces 142 facing each other are arranged in the locking portion 130. The number of the projection pieces 142 is not limited, but it is preferable that the number is smaller than the number of the outer circumferential planes of the distal connection portion 50 having the polygonal cross section. Specifically, the locking portion 130 has two projection pieces 142, for example. The projection piece 142 has a plate shape with a narrower width than the diameter of the distal connection portion 50.

The two projection pieces 142 are disposed at positions where the projection pieces 142 can respectively face the outer circumferential plane of the distal connection portion 50. More specifically, the two projection pieces 142 are disposed at positions which face each other at 180 degrees in the base 136 of the locking portion 130. However, the present invention is not limited to this example. The three projection pieces 142 may be equally arranged to face each other at an interval of 120 degrees. A facing interval between the projection pieces 142 is set to a dimension which enables the projection pieces 142 to come into close contact with or to move close to the outer circumferential plane of the distal connection portion 50.

If the distal connection portion 50 is connected to the clip 110 (clip body 110a), the plurality of the projection pieces 142 come into close contact with or move close to the distal connection portion 50 so as to surround the outer circumferential plane of the distal connection portion 50 accommodated in the accommodation portion 134. In this manner, if the distal connection portion 50 is rotated to generate torques, the outer circumferential plane of the distal connection portion 50 rotates the projection piece 142 around the axis, and the torques are applied to the overall clip body 110a via the locking portion 130.

The protruding portion 140 formed in the distal end on the proximally located side of the projection piece 142 is disposed on the circumference which is concentric with the base 136, and is formed in a partially arc shape. The individual protruding portion 140 has a partially arc shape whose central angle is approximately 120 degrees, and is formed so that the two protruding portions 140 can hold a region of approximately two thirds of the above-described circumference.

The base 136 has an annular shape formed by bending a plate material such as a metal material so that edges 138 abut on each other. The plurality of projection pieces 142 are arranged apart from each around the annular base 136.

As illustrated in FIGS. 3 and 11A, a joint of the abutted edges 138 is located at an intermediate position between the projection pieces 142 adjacent to each other.

A specific shape of the annular base 136 is not particularly limited, and can include an example such as a cylindrical shape, a prismatic shape, or a combination thereof. In addition, the base 136 may have an entirely annular shape in which joints of the edges 138 are in contact with each other, or may have a partially annular shape in which the joints of the edges 138 are separated at a predetermined interval.

A plurality of recesses 137 recessed toward the distally located side are formed in the peripheral edge on the proximal side of the base 136. The projection piece 142 is formed to project from a bottom portion 139 of the recess 137 to the proximal side. In this manner, the projection piece 142 can be formed long while the dimension of the locking portion 130 is restrained in the axial direction. When the distal connection portion 50 of the operation wire 20 is fitted to or removed from the accommodation portion 134, the projection piece 142 can be flexibly deformed.

Next, as illustrated in FIGS. 6 and 7A, the sheath 10 of the treatment instrument body 90 is an elongated and flexible cylindrical member. The sheath 10 is longer than the forceps hole of the endoscope used together with the clip device 100. For example, the sheath 10 can be configured to include a coil layer (not illustrated) around which a metal wire is wound long. An inner layer (not illustrated) made of fluorine-based polymer may be disposed on the inner peripheral surface of the coil layer. In addition, the sheath 10 may include a coil layer around which a resin wire is wound, or a flexible resin tube.

The inner diameter dimension of the sheath 10 has a size which slidably accommodates the centering portion 60 (FIG. 7A) disposed in the distal end of the operation wire 20. The clip 110 in a closed arm state can be accommodated inside the sheath 10 (refer to FIGS. 10B and 10C). Specifically, the inner diameter of the sheath 10 is 100 µm to 2,400 µm, for example. In addition, the thickness dimension of the sheath 10 is 100 µm to 350 µm, for example. In this manner, the flexibility of the sheath 10 can be improved.

The operation wire 20 is inserted into the sheath 10 so as to be movable forward and backward in the axial direction inside the sheath 10. For example, the operation wire 20 is formed of a highly rigid metal material such as stainless steel, a corrosion-resistant coated steel wire, titanium, or a titanium alloy. The metal material configuring the metal plate can include stainless steel, titanium, or a titanium alloy. However, the metal material is not limited thereto. In addition, the above-described metal member may be appropriately subjected to corrosion-resistant coating treatment. An outer layer (not illustrated) made of a fluorine-based polymer may be disposed on the outer peripheral surface of the operation wire 20.

For example, the distally located portion of the operation wire 20 has a centering portion 60, a strut 56, a distal connection portion 50, an elastic portion 80, and a diameter reduction sleeve 70.

The centering portion 60 has a block shape whose diameter is larger than that of the operation wire 20, and is fixed to the distally located portion of the operation wire 20. The centering portion 60 includes a cylinder-shaped portion (cylindrical portion), and the outer diameter of the cylindrical portion is formed to be equal to or slightly smaller than the inner diameter of the sheath 10. As the operation wire 20 moves forward and backward inside the sheath 10, the centering portion 60 moves forward and backward while sliding inside the sheath 10. In this case, since the outer diameter of the centering portion 60 is substantially the same as the inner diameter of the sheath 10, the operation wire 20 moves forward and backward while being positioned in the vicinity of the axis of the sheath 10. Even in a case where the sheath 10 is inserted into the forceps hole of the bent endoscope (not illustrated), since the operation wire 20 is positioned on substantially the center line of the forceps hole, a path length of the operation wire 20 is not changed, thereby restraining the distal connection portion 50 or the clip 110 from unexpectedly protruding from the sheath 10.

The strut 56 is formed coaxially with the operation wire 20 at a position on the distally located side from the centering portion 60, which is the distally located portion of the operation wire 20. The distal connection portion 50 is integrally formed in the distally located portion of the strut 56. A throttle portion 51 is formed between the strut 56 and the distal connection portion 50 (refer to FIG. 7A etc.). The elastic portion 80 is disposed around the strut 56 so as to accommodate the strut 56, and the distal connection portion 50 can be accommodated inside the diameter reduction sleeve 70.

A second inclined surface 54 is disposed in the distally located portion of the distal connection portion 50. In this manner, the distal connection portion 50 is pressed against the protruding portion 140 from the proximal side. Accordingly, the second inclined surface 54 causes the protruding portion 140 to be elastically deformed outward.

In addition, a first inclined surface 52 is disposed in the proximally located portion of the distal connection portion 50. In this manner, the operation wire 20 is pulled to the proximally located side in the forward/backward movement direction in a state where the distal connection portion 50 is accommodated in the accommodation portion 134. Accordingly, the first inclined surface 52 causes the protruding portion 140 to be deformed outward.

One or both of the first inclined surface 52 and the second inclined surface 54 may be a flat surface or a curved surface. In a case of the curved surface, the curved surface may be a projecting surface bulging outward in the radial direction so that the protruding portion 140 can be preferably spread outward.

At least one of the first inclined surface 52 and the second inclined surface 54 has a conical shape such as a truncated cone or a truncated pyramid.

More specifically, the first inclined surface 52 is a truncated conical surface whose diameter decreases toward the proximally located side, and the second inclined surface 54 is a truncated conical surface whose diameter decreases toward the distally located side.

The distally located portion of the operation wire 20 has a cylindrical sleeve (diameter reduction sleeve 70) which can be accommodated inside the sheath 10 and which accommodates the distal connection portion 50. The inner diameter of at least a portion of the diameter reduction sleeve 70 is smaller than the outer diameter of the locking portion 130 when the distal connection portion 50 is drawable from the accommodation portion 134.

The diameter reduction sleeve 70 is a member for restricting the clamping ring 150 in moving backward to the sheath 10 and switching the clip 110 (refer to FIG. 3) from an open arm state to a closed arm state (refer to FIGS. 11A and 11B). As illustrated in FIG. 7A, the diameter reduction sleeve 70 can be accommodated inside the sheath 10, and causes the operation wire 20 to move forward. In this manner, a portion (diameter enlargement portion 72) of the diameter reduction sleeve 70 can protrude from the sheath 10 (refer to FIG. 8B).

The sleeve (diameter reduction sleeve 70) has a diameter enlargement portion 72, a diameter reduction step portion 74, and a sleeve body 76. The diameter enlargement portion 72 is disposed on the distally located side in the diameter reduction sleeve 70, and is elastically self-openable. The diameter reduction step portion 74 is disposed on the proximally located side of the diameter enlargement portion 72. The sleeve body 76 is disposed on the proximally located side further from the diameter reduction step portion 74, and is more rigid in the radial direction than the diameter enlargement portion 72.

As illustrated in FIG. 9B, the inner diameter of the sleeve body 76 is smaller than the outer diameter of the locking portion 130 when the distal connection portion 50 is drawable from the accommodation portion 134. Therefore, in a state where the locking portion 130 and the distal connection portion 50 are connected to each other and the protruding portion 140 and the projection piece 142 are accommodated in the sleeve body 76, outward deformation of the projection piece 142 is restrained by the sleeve body 76. Therefore, the distal connection portion 50 is prevented from being separated from the accommodation portion 134.

However, at least a portion of the protruding portion 140 and the projection piece 142 is moved backward from the sleeve body 76. In this manner, the projection piece 142 can be sufficiently deformed, and the distal connection portion 50 can be drawn from the accommodation portion 134.

The diameter reduction step portion 74 is formed in a tapered shape whose diameter decreases toward the proximal side, between the sleeve body 76 and the diameter enlargement portion 72. A configuration material of the diameter reduction sleeve 70 is not limited to a specific material as long as the diameter of the member can decrease by an external force. For example, a metal material, or an elastomer such as a resin or rubber can be used.

The diameter reduction sleeve 70 is a cylindrical body (pipe) made of a metal material such as stainless steel, and has one or more slits (not illustrated) formed being cut out from the distally located portion toward the proximally located side of the diameter enlargement portion 72. The slit may be formed to have a length leading to the diameter reduction step portion 74. Since the slit is provided, at least the diameter enlargement portion 72 of the diameter reduction sleeve 70 is configured so that the diameter can be deformed to increase or the diameter can be deformed to decrease. As illustrated in FIG. 7A, in a state where the diameter reduction sleeve 70 is accommodated in the sheath 10 and is restrained by the sheath 10, the diameter of the diameter enlargement portion 72 is deformed to further decrease compared to a natural state where the diameter enlargement portion 72 is not restrained by the sheath 10 (FIG. 8B). Accordingly, the outer diameter of the diameter enlargement portion 72 is smaller the inner diameter of the sheath 10.

Then, as illustrated in each of FIG. 8B, the diameter enlargement portion 72 of the diameter reduction sleeve 70 protrudes from the sheath 10 to the distally located side. In this manner, the diameter enlargement portion 72 is elastically restored to the natural state. The diameter of the diameter enlargement portion 72 in the natural state is larger than the inner diameter of the sheath 10. In addition, the diameter of the sleeve body 76 in the natural state is smaller than the inner diameter of the sheath 10. The diameter reduction step portion 74 in the natural state has a larger diameter portion and a smaller diameter portion than the inner diameter of the sheath 10.

The elastic portion (transmission portion) 80 is a member for connecting the centering portion 60 and the diameter reduction sleeve 70 to each other, and is configured to be extendible in the axial direction.

The elastic portion 80 can be configured to include a coil around which a metal or a resin wire material is spirally wound, or an elastomer such as rubber. As the wire material, a metal wire of stainless steel or tungsten can be preferably used.

In a case of the present embodiment, the elastic portion 80 is configured to include the coil.

The elastic portion 80 is the coil wound at unequal pitches in which a winding pitch of both end portions respectively fixed to the centering portion 60 and the diameter reduction sleeve 70 is decreased and a winding pitch in the intermediate portion is increased compared to both end portions. More specifically, both end portions of the elastic portion 80 are closely wound so that adjacent winding loops are in contact with each other. The intermediate portion of the elastic portion 80 is wound at winding pitches in which the adjacent winding loops are separated from each other.

The diameter reduction sleeve 70 is a cylindrical member fixed to the elastic portion 80, and the operation wire 20, the elastic portion 80, and the diameter reduction sleeve 70 are arranged coaxially with the sheath 10. The sleeve body 76 of the diameter reduction sleeve 70 is accommodated in the elastic portion 80. The distally located portion of the elastic portion 80 is in contact with the proximally located side of the diameter reduction step portion 74. The distally located portion of the elastic portion 80 includes a stationary portion 82 fixed to the periphery of the sleeve body 76, and a movable portion 84 located on the distally located side of the stationary portion 82 and mounted on the periphery of the sleeve body 76 so as not to be fixed thereto. The stationary portion 82 is fixed to the periphery of the sleeve body 76 using an adhesive, a soldering metal wax, or by means of welding.

Hitherto, an example has been described where the distal portion of the operation wire 20 is connected (linked) to the proximal portion of the elastic portion 80 via the centering portion 60. However, the distal portion of the operation wire 20 may be directly connected (linked) to the proximal portion of the elastic portion 80.

As an example, the following structure can be adopted. A portion on the proximal side from the diameter reduction sleeve 70 in the elastic portion 80 configured to include the coil is spirally formed in a tapered shape in which the inner diameter and the outer diameter gradually decrease toward the proximal end of the elastic portion 80. In this case, for example, the inner diameter of the spirally-shaped portion is set to be equal to the outer diameter of the distal portion of the operation wire 20, and the inner peripheral surface of the spirally-shaped portion is joined to the outer peripheral surface of the distal portion of the operation wire 20. In this manner, the operation wire 20 and the elastic portion 80 can be connected to each other.

Hereinafter, the clip cartridge 200 will be described in detail.

As illustrated in FIG. 1, the clip cartridge 200 includes the inner case 30 and the outer case 40.

As illustrated in FIG. 5, the inner case 30 is configured so that a pair of inner case configuration components 31 are assembled to each other. The inner case 30 has a rectangular flat shape in a plan view, and internally has the first accommodation region 32 for accommodating the clip 110.

More specifically, the pair of inner case configuration components 31 are formed in mutually the same shape.

In addition, the outer case 40 is also configured so that a pair of outer case configuration components 41 are assembled to each other. The outer case 40 has an elongated and rectangular flat shape in a plan view, and internally has the second accommodation region 42 for accommodating the inner case 30.

More specifically, the pair of outer case configuration components 41 are formed in mutually the same shape.

As illustrated in FIGS. 1 and 2, the inner case configuration component 31 has a plate-shaped portion 311 having a rectangular flat-plate shape in a plan view.

The pair of inner case configuration components 31 are assembled to each other so that respective surfaces of the plate-shaped portions 311 face each other, thereby configuring the inner case 30.

The inner case configuration component 31 further has a side wall 315 disposed in one side end in the width direction of the plate-shaped portion 311 and erected from one surface of the plate-shaped portion 311. The side wall 315 extends in the forward/backward direction.

The inner case 30 is accommodated in the second accommodation region 42 so that one side wall 315 is disposed in one end in the width direction of the second accommodation region 42 and the other side wall 315 is disposed in the other end in the width direction of the second accommodation region 42 (refer to FIG. 4).

The plate-shaped portion 311 has a protruding portion 312 formed in a front end portion on one surface of the plate-shaped portion 311, and a hole portion 313 formed in the front end portion. The hole portion 313 is open at least on one surface of the plate-shaped portion 311. In a case of the present embodiment, the hole portion 313 penetrates the front and rear surfaces of the plate-shaped portion 311. Therefore, the hole portion 313 is open on both surfaces of the plate-shaped portion 311.

The protruding portion 312 and the hole portion 313 are arranged symmetrical to each other in the width direction. More specifically, in the protruding portion 312 and the hole portion 313, the hole portion 313 is disposed close to the side wall 315, and the protruding portion 312 is disposed on a side away from the side wall 315.

In a state where the pair of inner case configuration components 31 are assembled to each other, the protruding portion 312 of one inner case configuration component 31 is fitted into the hole portion 313 of the other inner case configuration component 31, and the protruding portion 312 of the other inner case configuration component 31 is fitted into the hole portion 313 of one inner case configuration component 31.

Furthermore, a recess 314 for accommodating the arm 120 of the clip 110 is formed on one surface of the plate-shaped portion 311. The recesses 314 are symmetrically formed in the width direction.

In a state where the pair of inner case configuration components 31 are assembled to each other, a facing interval of the pair of recesses 314 configures a portion of the first accommodation region 32, that is, a portion for accommodating the arm 120.

A ring holding recess 317 for holding the clamping ring 150 of the clip 110 in a fitted state is formed at a position adjacent to the proximal side of the recess 314 on one surface of the plate-shaped portion 311.

As illustrated in FIG. 2, the ring holding recess 317 is formed in a half-cylindrical shape (for example, a half-divided cylindrical shape), and is recessed from a bottom surface of the recess 314. The ring holding recess 317 is disposed on the proximal side of the central portion of the recess 314 in the width direction.

As illustrated in FIG. 2, an inclined surface 318 adjacent to the proximal side of the ring holding recess 317 is further formed on one surface of the plate-shaped portion 311. The inclined surface 318 is inclined so to become higher toward the proximal side.

A lower end of the inclined surface 318 intersects a rear end of the ring holding recess 317, and the inclined surface 318 extends to a position higher than the bottom surface of the recess 314.

Furthermore, a locking portion accommodation recess 319 adjacent to the proximal side of the inclined surface 318 is formed on one surface of the plate-shaped portion 311. The locking portion accommodation recess 319 is formed in a half-cylindrical shape (for example, a half-divided cylindrical shape), and is disposed at a position higher than the bottom surface of the recess 314.

Furthermore, on one surface of the plate-shaped portion 311, an adjacent wall 316 erected (protruded) in a direction the same as that of the side wall 315 is formed at a position adjacent to one side in the width direction with respect to the ring holding recess 317, the inclined surface 318, and the locking portion accommodation recess 319. The adjacent wall 316 is erected up to a height the same as that of the side wall 315. A rear end face of the adjacent wall 316 is disposed at a rear end position of the inner case configuration component 31.

The rear end surface of the adjacent wall 316 configures a forward movement restriction portion 322 which selectively restricts forward movement of the diameter reduction sleeve 70 in the diameter reduction sleeve 70 and the distal connection portion 50. That is, the inner case 30 has the forward movement restriction portion 322.

Furthermore, the plate-shaped portion 311 has a pair of slits 320 extending in the distal/proximal direction. One of the slits 320 is disposed on one side in the width direction from the ring holding recess 317, the inclined surface 318, the locking portion accommodation recess 319, and the adjacent wall 316. The other one of the slits 320 is disposed on the other side in the width direction from the ring holding recess 317, the inclined surface 318, the locking portion accommodation recess 319, and the adjacent wall 316.

For example, a front end of the pair of slits 320 is located in the vicinity of a front end of the recess 314, and a rear end of the slit 320 leads to a rear end of the inner case configuration component 31. Therefore, the pair of slits 320 are open backward.

Since the pair of slits 320 are formed in the plate-shaped portion 311, a portion interposed between the pair of slits 320 in the plate-shaped portion 311 configures a movable piece 321 which can be displaced in the thickness direction of the plate-shaped portion 311 by the elastically deformed plate-shaped portion 311.

Then, the movable piece 321 includes the ring holding recess 317, the inclined surface 318, the locking portion accommodation recess 319, and the adjacent wall 316.

In a state where the pair of inner case configuration components 31 are assembled to each other, the adjacent wall 316 overlaps the plate-shaped portion 311 serving as a counterpart in the thickness direction. Therefore, a notch-shaped portion 323 for avoiding interference with the distal portion of the adjacent wall 316 serving as a counterpart is formed in the movable piece 321.

As illustrated in FIGS. 1 and 4, there is provided a plate-shaped portion 411 formed in a rectangular flat plate shape in a plan view, which is elongated in the forward/backward direction.

The pair of outer case configuration components 41 are assembled to each other so that respective surfaces of the plate-shaped portions 411 face each other, thereby configuring the outer case 40.

A recess 424 for accommodating the inner case 30 is formed in a front portion on one surface of the plate-shaped portion 411. In a state where the pair of outer case configuration components 41 are assembled to each other, a facing interval between the pair of recesses 424 configures the second accommodation region 42.

The outer case 40 has a distal wall 421 disposed adjacent to a front side of the recess 424 and a pair of side walls 422 respectively disposed adjacent to both sides of the recess 424 in the width direction. Whereas the distal wall 421 extends in the width direction, the pair of side walls 422 respectively extend in the forward/backward direction. The distal wall 421 and the side wall 422 are respectively erected from one surface of the plate-shaped portion 411.

In a state where the pair of outer case configuration components 41 are assembled to each other, top surfaces of the distal walls 421 come into contact with each other.

The top surface of the distal wall 421 has a protruding portion 416 protruding toward the distal wall 421 serving as a counterpart. A rear surface side of the distal wall 421 has a notch-shaped portion 417 into which the protruding portion 416 serving as a counterpart is fitted, in a state where the pair of outer case configuration components 41 are assembled to each other. The protruding portion 416 and the notch-shaped portion 417 are arranged at mutually symmetrical positions in the width direction.

A protruding portion 414 and a hole portion 415 are formed in the rear end portion of the plate-shaped portion 411. The protruding portion 414 and the hole portion 415 are arranged at mutually symmetrical positions in the width direction.

The protruding portion 414 is formed in a state of further protruding from a raised portion 423 raised from one surface of the plate-shaped portion 411.

The hole portion 415 penetrates the front and rear surfaces of the raised portion 423 and the plate-shaped portion 411, and is formed in a shape into which the protruding portion 414 is fittable.

In a state where the pair of outer case configuration components 41 are assembled to each other, the protruding portion 414 is fitted into a root portion of the hole portion 415, and mutual facing surfaces (top surfaces) of the raised portions 423 come into contact with each other.

A protruding portion 412, a hole portion 429, a surrounding wall 425, a locking claw 428, a guide projection 413, and a hole portion 427 are arranged side by side on the rear side of the recess 424.

Among the protruding portion 412, the hole portion 429, the surrounding wall 425, the locking claw 428, the guide projection 413, and the hole portion 427, the protruding portion 412 is disposed on one end side in the width direction, and further protrudes from one surface of the plate-shaped portion 411 than the top surface of the side wall 422. The hole portion 427 penetrates the plate-shaped portion 411. The protruding portion 412 and the and the hole portion 427 are arranged at mutually symmetrical positions in the width direction.

In a state where the pair of outer case configuration components 41 are assembled to each other, the protruding portion 412 is fitted into the hole portion 427.

The guide projection 413 is disposed at a position adjacent to the hole portion 427 in the width direction, and protrudes from one surface of the plate-shaped portion 411 in a direction the same as that of the protruding portion 412. The guide projection 413 guides the protruding portion 412 toward the hole portion 427 when the pair of outer case configuration components 41 are assembled to each other.

The locking claw 428 is disposed closer to the center than the guide projection 413 in the width direction, and protrudes from one surface of the plate-shaped portion 411 in the direction the same as that of the protruding portion 412, and the distal end is bent in a hook claw shape.

The hole portion 429 penetrates the plate-shaped portion 411. The hole portion 429 and the locking claw 428 are arranged at mutually symmetrical positions in the width direction.

In a state where the pair of outer case configuration components 41 are assembled to each other, the locking claw 428 is fitted into and locked to the hole portion 429.

The surrounding wall 425 is disposed in the central portion in the width direction, and surrounds a distal opening of the insertion hole 43. The surrounding wall 425 is formed to be higher than the recess 424. A front surface of the surrounding wall 425 is formed to be flat, and faces forward.

In the outer case configuration component 41, a section where the protruding portion 412, the hole portion 429, the surrounding wall 425, the locking claw 428, the guide projection 413, and the hole portion 427 are arranged, and a section where the pair of raised portions 423 of the rear end portion are arranged are formed at a stage lower than that of the raised portion 423.

An intermediate protruding portion 426 is formed at an intermediate position in the forward/backward direction of this lower stage section. A height position of the top surface of the intermediate protruding portion 426 is equal to a height position of the top surface of the raised portion 423. In a state where the pair of outer case configuration components 41 are assembled to each other, the respective top surfaces of the pair of intermediate protruding portions 426 come into contact with each other.

For example, in the plate-shaped portion 411, the intermediate protruding portions 426 are respectively formed one by one at both side positions of the insertion hole configuration groove 418 (to be described later).

A notch-shaped portion 420 whose width increases backward and which has a V-shape in a plan view is formed in the central portion in the width direction of the rear end portion of the plate-shaped portion 411.

In the central portion in the width direction of one surface of the plate-shaped portion 411, a linear insertion hole configuration groove 418 is formed from the front end portion of the notch-shaped portion 420 through the front end of the surrounding wall 425.

The insertion hole configuration groove 418 extends in the axial direction. The insertion hole configuration groove 418 is formed in a half-cylindrical shape. In a state where the pair of outer case configuration components 41 are assembled to each other, the pair of insertion hole configuration grooves 418 are arranged to face each other, thereby forming the insertion hole 43 having a circular tube shape (refer to FIGS. 5 and 7A). In the present embodiment, the insertion hole 43 having a linear shape has been described as an example. However, the insertion hole 43 may be bent.

The insertion hole configuration groove 418 includes a groove body 418a which occupies most of the insertion hole configuration groove 418 in the longitudinal direction, and a widened portion 418b which is located on the front side of the groove body 418a and which is formed to be wider than the groove body 418a in the width direction.

The inner diameter of the groove body 418a (that is, the inner diameter of the insertion hole 43) is set to be slightly larger than the outer diameter of the sheath 10. When the sheath 10 is inserted into the insertion hole 43, the sheath 10 is guided forward along the peripheral wall of the insertion hole 43.

The front end portion of the insertion hole configuration groove 418 has a stopper configuration portion 419 which configures a stopper 44 (refer to FIGS. 5 and 7A) for restricting forward movement of the sheath 10.

The inner case configuration component 31 and the outer case configuration component 41 of the clip cartridge 200 are respectively configured as described above.

Then, the pair of inner case configuration components 31 are assembled to each other to configure the inner case 30 so that the clip 110 is in a state of being accommodated in the first accommodation region 32 formed therebetween (refer to FIGS. 5 and 7A).

Furthermore, the pair of outer case configuration components 41 are assembled to each other to configure the outer case 40 so that the inner case 30 is in a state of being accommodated in the second accommodation region 42 formed therebetween.

In this way, the clip cartridge 200 which internally holds the clip 110 is configured (refer to FIGS. 4, 5, and 7A).

Here, the protruding portion 312 and the hole portion 313 of the pair of inner case configuration components 31 are fitted to each other. That is, the inner case 30 is configured so that the pair of inner case configuration component 31 formed in mutually the same shape are assembled to each other, and the pair of inner case configuration components 31 are fitted to each other in a state of facing each other.

In addition, in the pair of outer case configuration components 41, the protruding portion 416 and the notch-shaped portion 417 are fitted to each other, the protruding portion 414 and the hole portion 415 are fitted to each other, the protruding portion 412 and the hole portion 427 are fitted to each other, and the locking claw 428 and the hole portion 429 are fitted to each other.

That is, the outer case 40 is configured so that the pair of outer case configuration component 41 formed in mutually the same shape are assembled to each other, and the pair of outer case configuration components 41 are fitted to each other in a state of facing each other.

In the width direction, the dimension of the inner case 30 is set slightly smaller than the inner dimension of the second accommodation region 42, and the inner case 30 is movable forward and backward inside the second accommodation region 42. More specifically, the outer surface of the pair of side walls 315 is guided to the inner surface of the side wall 422 of the outer case configuration component 41, and the inner case 30 is allowed to slide forward and backward with respect to the outer case 40.

In addition, the clamping ring 150 is pinched by the movable pieces 321 of the pair of inner case configuration components 31. More specifically, the clamping ring 150 is fitted into the pair of ring holding recesses 317. The rear end of the clamping ring 150 is restricted in moving backward by the pair of inclined surfaces 318.

In a case of the present embodiment, the pair of movable pieces 321 configure the pair of ring pinching portions.

Next, referring to each drawing in FIGS. 7A, 7B to 10A, 10B, and 10C, a series of procedures for connecting the distal connection portion 50 of the operation wire 20 to the clip 110 will be described.

Figure 7B:
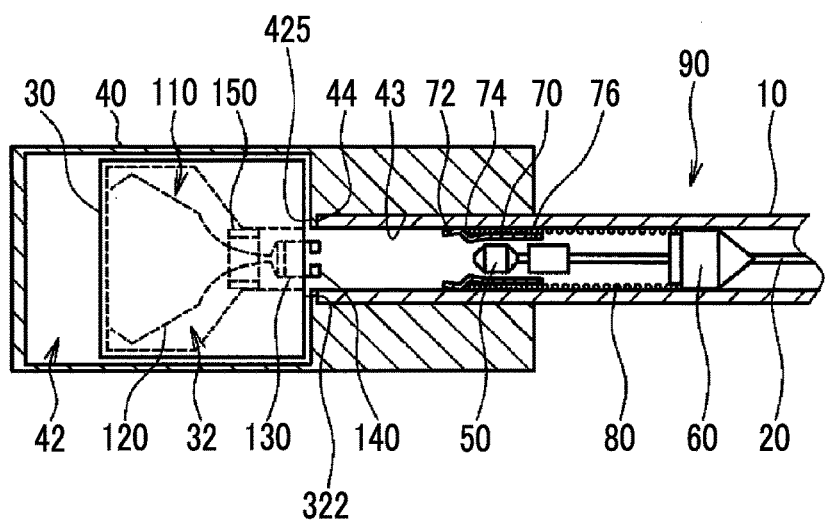
FIG. 7B is a schematic view for describing a mounted state in the series of operations for mounting the clip on the treatment instrument body of the endoscopic clip device.

First, as illustrated in FIGS. 7A and 7B, the sheath 10 of the treatment instrument body 90 is inserted into the insertion hole 43 of the outer case 40 of the clip cartridge 200 until the distal end of the sheath 10 abuts against the stopper 44.

Next, as illustrated in FIGS. 8A and 8B, the operation wire 20 is pressed. In this manner, the distal connection portion 50 and the diameter enlargement portion 72 of the diameter reduction sleeve 70 protrude from the sheath 10 to the distal side, and enter a region between the inner case 30 and the insertion hole 43 in the second accommodation region 42. The diameter enlargement portion 72 is elastically enlarged in diameter.

The diameter reduction sleeve 70 is restricted in further moving forward at a stage where the distal end of the diameter enlargement portion 72 abuts against the forward movement restriction portion 322. Thereafter, in the diameter reduction sleeve 70 and the distal connection portion 50, the distal connection portion 50 selectively moves forward.

Next, as illustrated in FIG. 8C, the operation wire 20 is further pressed. In this manner, the distal connection portion 50 moves forward relative to the diameter reduction sleeve 70. Accordingly, the distal connection portion 50 protrudes from the diameter reduction sleeve 70 to the distal side, thereby bringing the distal connection portion 50 and the locking portion 130 into a mutually connected state. The inner case 30 is slidable forward and backward relative to the outer case 40. Therefore, the inner case 30 moves forward relative to the outer case 40 when the operation wire 20 is pressed. However, the forward movement of the inner case 30 is restricted at the front end position of the second accommodation region 42.

Next, as illustrated in FIGS. 9A and 9B, if the operation wire 20 is pulled, while the proximal portion of the clip 110 is brought into a state of being drawn into the diameter reduction sleeve 70, the inner case 30 and the clip 110 are pulled close to sheath 10.

At this time, the clamping ring 150 presses the inclined surface 318 backward. In this manner, the inner case 30 moves backward, and the diameter reduction sleeve 70 is pressed and moved backward by the forward movement restriction portion 322 of the inner case 30.

In addition, while the pair of arms 120 of the clip 110 are slightly closed, the pair of arms 120 are drawn into the clamping ring 150. However, ligation is not performed.

As illustrated in FIGS. 9B to 10A, after the diameter reduction sleeve 70 moves backward until the diameter enlargement portion 72 comes into contact with the surrounding wall 425, the diameter enlargement portion 72 enters the sheath 10 while being reduced in diameter.

At this time, the inner case 30 moves backward relative to the outer case 40 inside the second accommodation region 42, and the inner case 30 presses the diameter reduction sleeve 70 backward. In this manner, the diameter enlargement portion 72 is drawn into the insertion hole 43 while being reduced in diameter.

Here, a magnitude of a force required for performing the ligation by causing the clamping ring 150 to close the pair of arms 120 is approximately 30 N to 50 N, for example. In contrast, a magnitude of a force F1 required for separating the clip 110 backward from the inner case 30 is approximately 10 N, for example. The force F1 is required for separating the clamping ring 150 backward from the ring pinching portion.

Therefore, the operation wire 20 is pulled using a force equal to or stronger than the force F1. In this manner, the clip 110 is drawn by the distal connection portion 50, and is moved backward after being separated from the inner case 30. However, the ligation is not performed. (refer to FIG. 10B).

Here, the magnitude of the force F2 required for drawing the diameter enlargement portion 72 of the diameter reduction sleeve 70 from the second accommodation region 42 into the sheath 10 is approximately 2 N to 3 N, for example.

In addition, the force F3 required for moving the inner case 30 backward relative to the outer case 40 in the second accommodation region 42 is sufficiently weaker than the force F2.

That is, the clip cartridge 200 is configured as follows. The operation wire 20 is pulled to the proximal side in the mutually connected state. In this manner, the clip 110 is drawn by the distal connection portion 50, and thus, the clip 110 is moved backward after being separated from the inner case 30. The force F1 required for separating the clip 110 from the inner case 30, the force F2 required for drawing the diameter enlargement portion 72 of the diameter reduction sleeve 70 from the second accommodation region 42 into sheath 10, and the force F3 required for moving the inner case 30 backward relative to the outer case 40 in the second accommodation region 42 satisfy a relationship of F1>F2>F3.

Accordingly, since the operation wire 20 pulls the inner case 30 via the clamping ring 150, while the inner case 30 is moved backward, the diameter enlargement portion 72 can be drawn into the sheath 10.

Figure 10B:
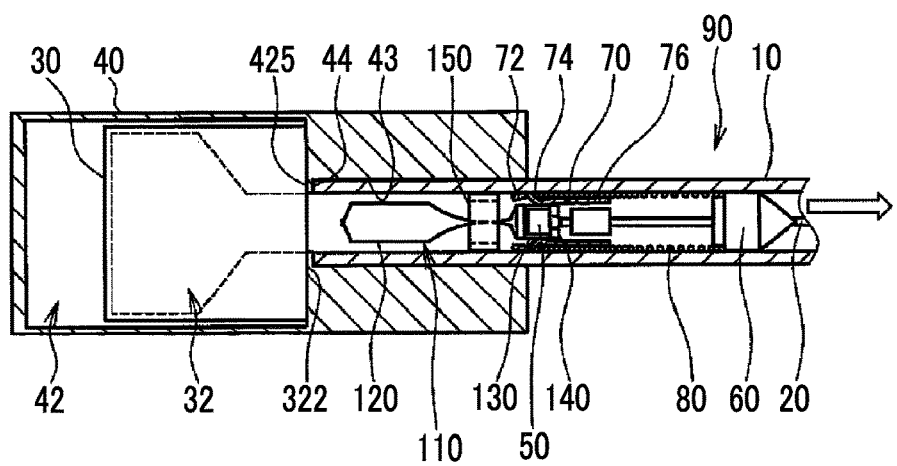
FIG. 10B is a schematic view for describing a series of operations for mounting the clip on the treatment instrument body of the endoscopic clip device.

As described above, the force of approximately 30 N to 50 N is required for fully ligating (finally clamping) the clip 110. Accordingly, before the final clamping, the diameter enlargement portion 72 of the diameter reduction sleeve 70 is reduced in diameter, and is accommodated in the sheath 10. Furthermore, before the final clamping, the clamping ring 150 and the clip 110 are accommodated in the sheath 10 (FIG. 10B).

Figure 10C:
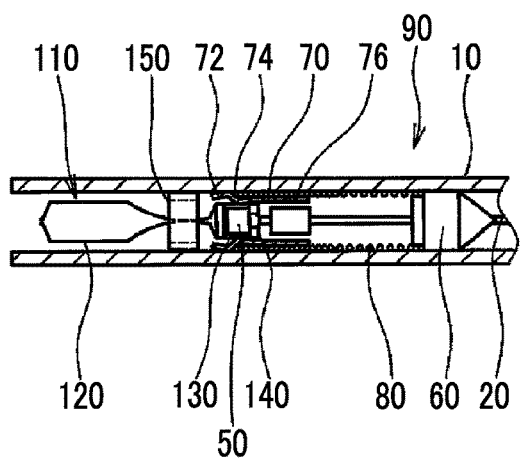
FIG. 10C is a schematic view for describing a series of operations for mounting the clip on the treatment instrument body of the endoscopic clip device.

Thereafter, the sheath 10 is drawn from the clip cartridge 200 (FIG. 10C). In the above-described manner, the clip 110 is completely mounted on the treatment instrument body 90.

Here, when the operation wire 20 is pulled to the proximal side in the mutually connected state, before the diameter enlargement portion 72 is drawn into sheath 10, the locking portion 130 and the distal connection portion 50 of the clip 110 is accommodated inside the sleeve body 76 of the diameter reduction sleeve 70 (refer to FIG. 9A). Accordingly, while the mutually connected state is maintained, the diameter enlargement portion 72 can be drawn into sheath 10.

More specifically, the clip 110 includes the clamping ring 150 into which the plurality of arms 120 are collectively inserted, and is configured so that the clamping ring 150 moves to the distal side of the arm 120 relative to the arm 120, thereby bringing the respective distal ends of the plurality of arms 120 into a mutually closed state.

The inner case 30 has the ring pinching portion (for example, the movable piece 321) which pinches the clamping ring 150, and the operation wire 20 is pulled to the proximal side in the mutually connected state. In this manner, the ring pinching portion is configured to be elastically deformed so that the clamping ring 150 is separated from the ring pinching portion.

Then, the force F1 is required for separating the clamping ring 150 from the ring pinching portion.

Here, the force required for separating the clamping ring 150 from the ring pinching portion is a resultant force of various forces required when the clamping ring 150 is separated from the ring pinching portion.

The force configuring the resultant force includes the force required for separating the clamping ring 150 from the ring pinching portion. This force is required for the following case. The clamping ring 150 is pulled to the proximal side. In this manner, for example, while a facing interval of the pair of movable pieces 321 is spread, the clamping ring 150 is allowed to frictionally slide relative to the pair of movable pieces 321 and to move to the proximal side.

Furthermore, the resultant force includes the force required for separating the clip 110 from the first accommodation region 32 to the proximal side. That is, the arm 120 of the clip 110 has the self-openable force. Accordingly, when the clip 110 is separated backward from the first accommodation region 32, frictional resistance (resistance force) caused by the self-openable force is generated between the arm 120 and the inner wall surface of the first accommodation region 32 in the inner case 30. Therefore, this resistance force is also included in the resultant force.

In addition to these forces, the resultant force includes a force caused by friction of each unit.

More specifically, the ring pinching portion has the ring holding recess 317 which holds the clamping ring 150 in a fitted state, and the inclined surface 318 adjacent to the proximal side of the ring holding recess 317, which is the inclined surface 318 inclined in a direction where the facing interval of the ring pinching portions is narrowed toward the proximal side.

More specifically, the inner case 30 has the inner case body (for example, the portion excluding the movable piece 321 in the inner case configuration component 31) and the ring pinching portion. The ring pinching portion includes the movable piece 321 supported in a cantilevered manner by the inner case body (in the present embodiment, the movable piece 321 itself is the ring pinching portion).

Then, when the operation wire 20 is pulled to the proximal side in the mutually connected state, the movable piece 321 is elastically displaced in the direction where the facing interval of the ring pinching portions (that is, the movable pieces 321) is widened, thereby separating the clamping ring 150 from the inner case 30. That is, the pair of movable pieces 321 are elastically deformed in direction away from each other. In this manner, the clamping ring 150 is separated from the inner case 30.

Here, as illustrated in FIG. 5, in the movable piece 321, the outer surface 324 facing the inner surface of the outer case 40 is inclined in a direction away from the inner surface of the outer case 40 toward the proximal side. In this manner, between the outer surface 324 and the inner surface of the outer case 40, a space is secured for the pair of movable pieces 321 to be elastically displaced in the direction where the facing interval of the pair of movable pieces 321 is widened.

Next, a series of procedures will be described in which the clip 110 is closed and the clip 110 is further separated from the distal connection portion 50.

As illustrated in FIG. 10C, in a state where the clip 110 is accommodated in the sheath 10, the sheath 10 is caused to penetrate into the body lumen through the forceps hole of the endoscope. If the distally located side portion of the sheath 10 reaches the vicinity of the living body tissue requiring the ligation, the operation wire 20 is pressed to the distally located side. In this manner, the clip 110 and the clamping ring 150 protrude from the distal end of the sheath 10. The clip 110 is naturally spread to have the maximum opening width by the self-openable force.

In this case, at least the diameter enlargement portion 72 and the diameter reduction step portion 74 in the diameter reduction sleeve 70 protrude from a distally located opening of the sheath 10, and are deformed to have the diameter in the natural state. Next, the position and the orientation of the clip 110 are adjusted with respect to the living body tissue to be ligated.

If the treatment instrument body 90 (refer to FIG. 1) is rotated to generate torques, the operation wire 20 and the distal connection portion 50 are rotated to generate the torques in conjunction with each other. Furthermore, since the distal connection portion 50 transmits the torques to the locking portion 130, the arm 120 of the clip 110 is also rotated to generate the torques. In this manner, the opening direction of the arm 120 can be oriented in a desired direction with respect to a ligation site of the living body tissue.

After the position and the orientation of the clip 110 are determined, the operation wire 20 is drawn to the proximally located side in a state where the distal end of the clip 110 is pressed against the ligation site. The clamping ring 150 comes into contact with the inner surface of the diameter reduction step portion 74, and is fitted into the diameter enlargement portion 72, thereby restricting the backward movement to the diameter reduction sleeve 70 and the sheath 10. In addition, the clamping ring 150 is fitted to the diameter enlargement portion 72. Accordingly, even if an external force is applied to the diameter enlargement portion 72, the diameter enlargement portion 72 is restrained from being deformed to decrease the diameter. Even if the operation wire 20 is drawn to the proximally located side with a strong force, the diameter enlargement portion 72 is prevented from being drawn into the sheath 10.

The operation wire 20 and the diameter reduction sleeve 70 are connected to each other by the elastic portion 80. Therefore, even after the diameter reduction sleeve 70 is restricted in moving to the proximally located side relative to the clip device 100, the operation wire 20 is drawn to the proximally located side. In this manner, the elastic portion 80 extends, and the distal connection portion 50 can be further drawn to the proximally located side inside the sheath 10.

The operation wire 20 is pulled to the proximally located side in the forward/backward movement direction in a state where the distal connection portion 50 is accommodated in the accommodation portion 134. In this manner, the arms 120 are closed (refer to FIGS. 11A and 11B) so as to grip the living body tissue. Drawing the operation wire 20 is stopped while the arms 120 are closed, and the operation wire 20 is pressed again, thereby enabling the arms 120 to be opened again. Then, after the optimum ligation is confirmed, if the operation wire 20 is drawn to the proximally located side again, the clamping ring 150 is fitted to the narrowed portion 123 disposed in the arm 120 so as to lock the clip 110. In this manner, the clip 110 is brought into a closed arm state.

When the arms 120 are closed so as to grip the living body tissue, the protruding portion 140 of the locking portion 130 is accommodated inside the diameter reduction sleeve 70. In this state, the operation wire 20 is further pulled to the proximally located side. In this manner, the protruding portion 140 protrudes to the proximal side from the sleeve body 76 of the diameter reduction sleeve 70, and can be greatly deformed outward. Here, the description that the protruding portion 140 is greatly deformed means that the protruding portion 140 is deformed to have a large diameter until at least the distal connection portion 50 is drawable from the accommodation portion 134.

Therefore, when the living body tissue is ligated, an operation for moving the slider 94 backward is continuously performed, and the slider 94 is further moved backward, thereby removing the distal connection portion 50 from the locking portion 130. In this manner, the clip 110 is separated from the operation wire 20, and is caused to indwell the body lumen in a state where living body tissue is ligated.

According to the above-described configuration, a series of procedures is completed from when the distal connection portion 50 is connected to the clip 110 so as to close the clip 110 until the distal connection portion 50 is further separated from the clip 110. The above described procedures are repeatedly performed, thereby enabling multiple clips 110 to ligate the living body tissue.

Unlike the technology disclosed in PTL 1, a series of procedures can be easily performed since the series of procedures do not include work for collecting and detaching the broken connection member.

According to the above-described embodiment, the operation wire 20 is pressed forward in a state where the treatment instrument body 90 is inserted into the insertion hole 43. In this manner, the distal connection portion 50 and the diameter enlargement portion 72 of the sleeve protrude from the sheath 10 to the distal side, and enter a region between the inner case 30 and the insertion hole 43 in the second accommodation region 42. The diameter enlargement portion 72 is elastically enlarged in diameter.

Then, the operation wire 20 is further pressed forward so that the distal connection portion 50 moves forward relative to the sleeve. In this manner, the distal connection portion 50 protrudes from the sleeve to the distal side, and the distal connection portion 50 and the locking portion 130 are brought into the mutually connected state.

In addition, the operation wire 20 is pulled to the proximal side in the mutually connected state. In this manner, the inner case 30 moves backward relative to the outer case 40 inside the second accommodation region 42, and the inner case 30 presses the sleeve backward. In this manner, the diameter enlargement portion 72 is drawn into the sheath 10 while being reduced in diameter.

Accordingly, the clip 110 having a structure enabling a user to easily perform the series of procedures can be easily and reliably mounted on the treatment instrument body 90.

The present invention is not limited to the above-described embodiment, and includes various modifications and improvements as long as the object of the present invention is achieved.

For example, in the above-described embodiment, an example has been described in which the distal connection portion 50 has the block shape and is accommodated in the claw-shaped locking portion 130 in the proximal end of the clip 110. However, in contrast to this example, the locking portion 130 in the proximal end of the clip 110 may be held and enclosed by the distal connection portion 50 formed in a claw shape.

Various configuration elements of the clip cartridge 200 according to the present invention do not need to exist individually and independently. The present invention allows that a plurality of configuration elements are formed as a single member, that one element is formed of a plurality of members, that a certain configuration element is a portion of the other configuration element, and that a portion of a certain configuration element overlaps a portion of the other configuration element.

The above-described embodiment includes the following technical concept.

(1) There is a clip cartridge used for connecting a clip to an elongated treatment instrument body holding a clip. The clip includes a plurality of arms for gripping a living body tissue and a clip body having a locking portion disposed on a proximal side of the arms. The treatment instrument body has an elongated sheath, an operation wire which is inserted into the sheath so as to be movable forward and backward and in which a distal connection portion is disposed in a distally located portion, a cylindrical sleeve which is capable of being accommodated inside the sheath and which accommodates the distal connection portion, and a transmission portion which transmits a forward movement force and a backward movement force from the operation wire to the sleeve. The sleeve has a diameter enlargement portion which is elastically self-openable, and a cylindrical sleeve body which is disposed on a proximally located side from the diameter enlargement portion and whose radial rigidity is higher than that of the diameter enlargement portion. The clip cartridge includes an inner case that has a first accommodation region for accommodating the clip, and an outer case that has an elongated insertion hole into which the treatment instrument body is inserted, and a second accommodation region which communicates with a distal end of the insertion hole and which accommodates the inner case so as to be movable to a distal side and a proximal side. In a state where the treatment instrument body is inserted into the insertion hole, the operation wire is pressed forward so that the distal connection portion and the diameter enlargement portion of the sleeve protrude from the sheath to a distal side and enter a region between the inner case in the second accommodation region and the insertion hole, and so that the diameter enlargement portion is elastically enlarged in diameter. The operation wire is further pressed forward so that the distal connection portion moves forward relative to the sleeve, thereby causing the distal connection portion to protrude from the sleeve to the distal side and bringing the distal connection portion and the locking portion into a mutually connected state. The operation wire is pulled to a proximal side in the mutually connected state so that the inner case moves backward relative to the outer case inside the second accommodation region and the inner case presses the sleeve backward, thereby drawing the diameter enlargement portion into the sheath while reducing the diameter enlargement portion in diameter.

(2) In the clip cartridge according to (1) described above, the operation wire is pulled to the proximal side in the mutually connected state so that the clip is drawn by the distal connection portion, thereby separating the clip from the inner case and causing the clip to move backward. In a case of setting a force F1 required for separating the clip from the inner case, a force F2 required for drawing the diameter enlargement portion of the sleeve into the sheath from the second accommodation region, and a force F3 required for moving the inner case backward relative to the outer case in the second accommodation region, a relationship of F1>F2>F3 is satisfied.

(3) In the clip cartridge according to (2) described above, the clip further includes a clamping ring into which the plurality of arms are collectively inserted, and is configure so that the clamping ring moves to a distal side of the arm relative to the arm, thereby bringing the respective distal ends of the plurality of arms into a mutually closed state. The inner case has a ring pinching portion which pinches the clamping ring, and the operation wire is pulled to the proximal side in the mutually connected state so that the ring pinching portion is elastically deformed and the clamping ring is separated from the ring pinching portion. The force F1 represents a force required when the clamping ring is separated from the ring pinching portion.

(4) In the clip cartridge according to (3) described above, the ring pinching portion has a ring holding recess which holds the clamping ring in a fitted state, and an inclined surface which is adjacent to a proximal side of the ring holding recess and which is inclined toward the proximal side in a direction where a facing interval of the ring pinching portion is narrowed.

(5) In the clip cartridge according to (3) or (4) described above, the inner case has an inner case body and the ring pinching portion. The ring pinching portion includes a movable piece which is supported by the inner case body in a cantilever manner. When the operation wire is pulled to the proximal side in the mutually connected state, the movable piece is elastically displaced in a direction where a facing interval of the ring pinching portion is widened, thereby separating the clamping ring from the inner case.

(6) In the clip cartridge according to (5) described above, in the movable piece, an outer surface which faces an inner surface of the outer case is inclined in a direction away from the inner surface of the outer case toward the proximal side.

(7) In the clip cartridge according to any one of (1) to (6) described above, the inner case has a forward movement restriction portion which selectively restricts forward movement of the sleeve.

(8) In the clip cartridge according to any one of (1) to (7) described above, the inner case is configured by combining a pair of inner case configuration components formed in the same shape with each other. The pair of inner case configuration components are fitted to each other in a mutually facing state.

(9) In the clip cartridge according to any one of (1) to (8), the outer case is configured by combining a pair of outer case configuration components formed in the same shape with each other. The pair of outer case configuration components are fitted to each other in a mutually facing state.

(10) In the clip cartridge according to any one of (1) to (9), when the operation wire is pulled to the proximal side in the mutually connected state, before the diameter enlargement portion is drawn into the sheath, the locking portion of the clip and the distal connection portion is accommodated inside the sleeve body of the sleeve.

INDUSTRIAL APPLICABILITY

According to the present invention, a clip having a structure enabling a user to easily perform a series of procedures can be easily and reliably mounted on an endoscope body.

REFERENCE SIGNS LIST

10 SHEATH
20 OPERATION WIRE
30 INNER CASE
31 INNER CASE CONFIGURATION COMPONENT
32 FIRST ACCOMMODATION REGION
311 PLATE-SHAPED PORTION
312 PROTRUDING PORTION
313 HOLE PORTION
314 RECESS

315 SIDE WALL
316 ADJACENT WALL
317 RING HOLDING RECESS
318 INCLINED SURFACE
319 LOCKING PORTION ACCOMMODATION RECESS
320 SLIT
321 MOVABLE PIECE
322 FORWARD MOVEMENT RESTRICTION PORTION
323 NOTCH-SHAPED PORTION
324 OUTER SURFACE
40 OUTER CASE
41 OUTER CASE CONFIGURATION COMPONENT
42 SECOND ACCOMMODATION REGION
43 INSERTION HOLE
44 STOPPER
411 PLATE-SHAPED PORTION
412 PROTRUDING PORTION
413 GUIDE PROJECTION
414 PROTRUDING PORTION
415 HOLE PORTION
416 PROTRUDING PORTION
417 NOTCH-SHAPED PORTION
418 INSERTION HOLE CONFIGURATION GROOVE
418a GROOVE BODY
418b WIDENED PORTION
419 STOPPER CONFIGURATION PORTION
420 NOTCH-SHAPED PORTION
421 DISTAL WALL
422 SIDE WALL
423 RAISED PORTION
424 RECESS
425 SURROUNDING WALL
426 INTERMEDIATE PROTRUDING PORTION
427 HOLE PORTION
428 LOCKING CLAW
429 HOLE PORTION
50 DISTAL CONNECTION PORTION
51 THROTTLE PORTION
52 FIRST INCLINED SURFACE
54 SECOND INCLINED SURFACE
56 STRUT
60 CENTERING PORTION
70 DIAMETER REDUCTION SLEEVE (SLEEVE)
72 DIAMETER ENLARGEMENT PORTION
74 DIAMETER REDUCTION STEP PORTION
76 SLEEVE BODY
80 ELASTIC PORTION (TRANSMISSION PORTION)
82 STATIONARY PORTION
84 MOVABLE PORTION
90 TREATMENT INSTRUMENT BODY
92 FINGER RING
94 SLIDER
96 MAIN BODY SHAFT
100 ENDOSCOPIC CLIP DEVICE
110 CLIP
110a CLIP BODY
120 ARM
121 WIDENED PORTION
122 PROXIMAL PORTION
123 NARROWED PORTION
124 ARM BODY
125 REINFORCEMENT PORTION
126 CLAW
130 LOCKING PORTION
132 SPACE
134 ACCOMMODATION PORTION
136 BASE
137 RECESS
138 EDGE
139 BOTTOM PORTION
140 PROTRUDING PORTION
142 PROJECTION PIECE
150 CLAMPING RING
200 CLIP CARTRIDGE

The invention claimed is:

1. A clip cartridge system, comprising:
an elongated treatment instrument body;
a clip comprising a clip body having a plurality of arms and a locking portion positioned on a proximal side of the arms such that the plurality of arms grips a living body; and
a clip cartridge configured to connect the clip to the elongated treatment instrument body and comprising an inner case having a first accommodation region, and an outer case having a second accommodation region and an elongated insertion hole such that the first accommodation region accommodates the clip with the plurality of arms opened, that the elongated treatment instrument body is inserted into the elongated insertion hole, that the second accommodation region communicates with a distal end of the elongated insertion hole, and that the inner case is accommodated in the second accommodation region so as to move between a distal side and a proximal side of the second accommodation region with the plurality of arms opened,
wherein the elongated treatment instrument body has an elongated sheath, an operation wire inserted into the elongated sheath so as to move forward and backward, a distal connection portion disposed in a distally located portion of the operation wire, a cylindrical sleeve accommodated inside the elongated sheath and configured to accommodate the distal connection portion, and a transmission portion which transmits a forward movement force and a backward movement force from the operation wire to the cylindrical sleeve, the cylindrical sleeve has a diameter enlargement portion which is elastically self-openable, and a cylindrical sleeve body disposed on a proximally located side from the diameter enlargement portion and whose radial rigidity is higher than a radial rigidity of the diameter enlargement portion, in a state where the elongated treatment instrument body is inserted into the elongated insertion hole, the operation wire is pressed forward such that the distal connection portion and the diameter enlargement portion of the cylindrical sleeve protrude from the elongated sheath to a distal side and enter a region between the inner case in the second accommodation region and the insertion hole, and that the diameter enlargement portion is elastically enlarged in diameter, when the operation wire is further pressed forward such that the distal connection portion moves forward relative to the cylindrical sleeve, the distal connection portion protrudes from the cylindrical sleeve to the distal side, and the distal connection portion and the locking portion are brought into a mutually connected state, and when the operation wire is pulled to a proximal side in the mutually connected state such that the inner case moves backward relative to the outer case inside the second accommodation region and the inner case presses the cylindrical sleeve backward, the diameter enlargement portion is drawn into the elongated sheath while the diameter enlargement portion is reduced in diameter.

2. The clip cartridge system according to claim 1, wherein when the operation wire is pulled to the proximal side in the mutually connected state such that the clip is drawn by the distal connection portion, the clip is separated from the inner case and is caused to move backward, and in a case of setting a force F1 required for separating the clip from the inner case, a force F2 required for drawing the diameter enlargement portion of the cylindrical sleeve into the elongated sheath from the second accommodation region, and a force F3 required for moving the inner case backward relative to the outer case in the second accommodation region, a relationship of F1>F2>F3 is satisfied.

3. The clip cartridge system according to claim 2, wherein the clip further includes a clamping ring into which the plurality of arms are collectively inserted, and is configured such that the clamping ring moves to a distal side of the arms relative to the arms and brings distal ends of the plurality of arms into a mutually closed state, the inner case has a ring pinching portion which pinches the clamping ring, the ring pinching portion is configured to be elastically deformed when the operation wire is pulled to the proximal side in the mutually connected state such that the clamping ring is separated from the ring pinching portion, and the force F1 represents a force required when the clamping ring is separated from the ring pinching portion.

4. The clip cartridge system according to claim 3, wherein the ring pinching portion has a ring holding recess configured to hold the clamping ring in a fitted state, and an inclined surface adjacent to a proximal side of the ring holding recess and inclined toward the proximal side in a direction where a facing interval of the ring pinching portion is narrowed.

5. The clip cartridge system according to claim 4, wherein the inner case has an inner case body and the ring pinching portion, the ring pinching portion includes a movable piece supported by the inner case body in a cantilever manner, and when the operation wire is pulled to the proximal side in the mutually connected state, the movable piece is elastically displaced in a direction where a facing interval of the ring pinching portion is widened, and the clamping ring is separated from the inner case.

6. The clip cartridge system according to claim 5, wherein the movable piece has an outer surface which faces an inner surface of the outer case and which is inclined in a direction away from the inner surface of the outer case toward the proximal side.

7. The clip cartridge system according to claim 3, wherein the inner case has an inner case body and the ring pinching portion, the ring pinching portion includes a movable piece supported by the inner case body in a cantilever manner, and when the operation wire is pulled to the proximal side in the mutually connected state, the movable piece is elastically displaced in a direction where a facing interval of the ring pinching portion is widened, and the clamping ring is separated from the inner case.

8. The clip cartridge system according to claim 7, wherein the movable piece has an outer surface which faces an inner surface of the outer case and which is inclined in a direction away from the inner surface of the outer case toward the proximal side.

9. The clip cartridge system according to claim 3, wherein the inner case has a forward movement restriction portion which selectively restricts forward movement of the cylindrical sleeve.

10. The clip cartridge system according to claim 3, wherein the inner case comprises a pair of inner case configuration components having the same shape and fitted to each other in a mutually facing state.

11. The clip cartridge system according to claim 3, wherein the outer case comprises a pair of outer case configuration components having the same shape and fitted to each other in a mutually facing state.

12. The clip cartridge system according to claim 3, wherein when the operation wire is pulled to the proximal side in the mutually connected state, before the diameter enlargement portion is drawn into the elongated sheath, the locking portion of the clip and the distal connection portion of the elongated treatment instrument body is accommodated inside the cylindrical sleeve body of the cylindrical sleeve.

13. The clip cartridge system according to claim 2, wherein the inner case has a forward movement restriction portion which selectively restricts forward movement of the cylindrical sleeve.

14. The clip cartridge system according to claim 2, wherein the inner case comprises a pair of inner case configuration components having the same shape and fitted to each other in a mutually facing state.

15. The clip cartridge system according to claim 2, wherein the outer case comprises a pair of outer case configuration components having the same shape and fitted to each other in a mutually facing state.

16. The clip cartridge system according to claim 2, wherein when the operation wire is pulled to the proximal side in the mutually connected state, before the diameter enlargement portion is drawn into the elongated sheath, the locking portion of the clip and the distal connection portion of the elongated treatment instrument body is accommodated inside the cylindrical sleeve body of the cylindrical sleeve.

17. The clip cartridge system according to claim 1, wherein the inner case has a forward movement restriction portion which selectively restricts forward movement of the cylindrical sleeve.

18. The clip cartridge system according to claim 1, wherein the inner case comprises a pair of inner case configuration components having the same shape and fitted to each other in a mutually facing state.

19. The clip cartridge system according to claim 1, wherein the outer case comprises a pair of outer case configuration components having the same shape and fitted to each other in a mutually facing state.

20. The clip cartridge system according to claim 1, wherein when the operation wire is pulled to the proximal side in the mutually connected state, before the diameter enlargement portion is drawn into the elongated sheath, the locking portion of the clip and the distal connection portion of the elongated treatment instrument body is accommodated inside the cylindrical sleeve body of the cylindrical sleeve.

* * * * *